United States Patent
Niu et al.

(10) Patent No.: US 9,200,286 B2
(45) Date of Patent: Dec. 1, 2015

(54) SUBUNIT-SELECTIVE NUCLEIC ACID INHIBITORS OF GLUTAMATE RECEPTORS

(75) Inventors: Li Niu, Loudonville, NY (US); Zhen Huang, Latham, NY (US); Jae Seon Park, Seoul (KR)

(73) Assignee: THE RESEARCH FOUNDATION FOR THE STATE UNIVERSITY OF NEW YORK, Albany, NY (US)

( * ) Notice: Subject to any disclaimer, the term of this patent is extended or adjusted under 35 U.S.C. 154(b) by 0 days.

(21) Appl. No.: 13/810,572

(22) PCT Filed: Jul. 15, 2011

(86) PCT No.: PCT/US2011/044206
§ 371 (c)(1),
(2), (4) Date: Jun. 28, 2013

(87) PCT Pub. No.: WO2012/047355
PCT Pub. Date: Apr. 12, 2012

(65) Prior Publication Data
US 2013/0289100 A1    Oct. 31, 2013

Related U.S. Application Data

(60) Provisional application No. 61/365,020, filed on Jul. 16, 2010.

(51) Int. Cl.
*C07H 21/04* (2006.01)
*C12N 15/115* (2010.01)
*C12N 15/11* (2006.01)
*C12N 15/113* (2010.01)

(52) U.S. Cl.
CPC ............ *C12N 15/115* (2013.01); *C12N 15/111* (2013.01); *C12N 15/1138* (2013.01); *C12N 2310/16* (2013.01); *C12N 2310/322* (2013.01); *C12N 2310/3533* (2013.01); *C12N 2320/13* (2013.01)

(58) Field of Classification Search
None
See application file for complete search history.

(56) References Cited

U.S. PATENT DOCUMENTS

2003/0175730 A1*  9/2003  Shi et al. .................... 435/6

OTHER PUBLICATIONS

Huang Zhen et al; "RNA aptamers selected against the GluR2 glutamate receptor channel," Nov. 2007, Biochemistry, vol. 46, Nr. 44, pp. 12648-12655.
Park Jae-Seon et al; "Potent and Selective Inhibition of a Single alpha-Amino-3-hydroxy-5-methyl-4-isoxazolepropionic Acid (AMPA) Receptor Subunit by an RNA Aptamer," Apr. 2011, Journal of Biological Chemistry, vol. 286, Nr. 17, pp. 15608-15617.

* cited by examiner

*Primary Examiner* — Kimberly Chong
(74) *Attorney, Agent, or Firm* — Heslin Rothenberg Farley & Mesiti P.C.; Kathy Smith Dias, Esq.

(57) ABSTRACT

Inhibitors of AMPA-type glutamate ion channels are useful as biochemical probes for structure-function studies and as drug candidates for a number of neurological disorders and diseases. Disclosed herein is the identification of an RNA inhibitor or aptamer by an in vitro evolution approach and characterization of its mechanism of inhibition on the sites of interaction by equilibrium binding and on the receptor channel-opening rate by a laser-pulse photolysis technique. The aptamer of the invention is a noncompetitive inhibitor of AMPA-type glutamate ion channels, one that selectively inhibits the GluA2Q$_{flip}$ AMPA receptor subunit without any effect on other AMPA receptor subunits or on kainate or NMDA receptors. Furthermore, the aptamer preferentially inhibits the closed-channel state of GluA2Q$_{flip}$ with a $K_I$=1.5 µM or by ~15-fold over the open-channel state. The potency and selectivity of this aptamer rival those of small molecule inhibitors. Together, these properties make the aptamers of the present invention promising water-soluble, highly potent, GluA2 subunit-selective drugs.

20 Claims, 15 Drawing Sheets

A

B

A

B

| SEQ ID. NO. | NUCLEOTIDE SEQUENCE | DESIGNATION | # NT |
|---|---|---|---|
| 1 | GGGAGAAUUC AACUGCCAUC UAGGCAGAAG UGUAAUAGCC AACGGUGCCA GUCCGAAACG GAUCGUUAGA GCAUCAGUAC UACAAGCUUC UGGACUCGGU | AF1422 | 100 |
| 2 | GGGAGAAUUC AACUGCCAUC UAGCCAGAAG UGUAAUAGCC AAUACUACAA GCUUCUGGAC UCGGU | AF65 | 65 |
| 3 | GGGAGCCAGA AGUGUAAUAG CCAACGGUGC CAGUCCGAAAC GGAUCGUUA GAGCAUCAGU ACUACAAGCU UCUGGACU | AF78 | 78 |
| 4 | GGGAGAAUUC AACUGCCACG GAUAAUAGCC AAUACUACAA CCGU | AF44 | 44 |
| 5 | GGGAACGGUG CCAGUCCGAA ACGGAUCGUU AGAGCAUCAG UA | AF42 | 42 |
| 6 | GGGUCGUUAG AGCAUCAGUA CACCAACGGU GCGAGCCC | AF38 | 38 |
| 7 | GGGAGAAUUC AACUGCCAUC | AF20 | 20 |

FIGURE 15

SEQUENCE LISTING

<160> NUMBER OF SEQ ID NOS: 7

<210> SEQ ID NO 1
<211> LENGTH: 100
<212> TYPE: RNA
<213> ORGANISM: Artificial Sequence
<220> FEATURE:
<223> OTHER INFORMATION: Synthetic oligonucleotide

<400> SEQUENCE: 1
gggagaauuc aacugccauc uaggcagaag uguaauagcc aacggugcca guccgaaacg        60
gaucguuaga gcaucaguac uacaagcuuc uggacucggu                            100

<210> SEQ ID NO 2
<211> LENGTH: 65
<212> TYPE: RNA
<213> ORGANISM: Artificial Sequence
<220> FEATURE:
<223> OTHER INFORMATION: Synthetic Oligonucleotide

<400> SEQUENCE: 2
gggagaauuc aacugccauc uagccagaag uguaauagcc aauacuacaa gcuucuggac        60
ucggu                                                                   65

<210> SEQ ID NO 3
<211> LENGTH: 78
<212> TYPE: RNA
<213> ORGANISM: Artificial Sequence
<220> FEATURE:
<223> OTHER INFORMATION: Synthetic oligonucleotide

<400> SEQUENCE: 3
gggagccaga aguguaauag ccaacggugc caguccgaaa cggaucguua gagcaucagu        60
acuacaagcu ucuggacu                                                     78

<210> SEQ ID NO 4
<211> LENGTH: 44
<212> TYPE: RNA
<213> ORGANISM: Artificial Sequence
<220> FEATURE:
<223> OTHER INFORMATION: Synthetic Oligonucleotide

<400> SEQUENCE: 4
gggagaauuc aacugccacg gauaauagcc aauacuacaa ccgu                        44

<210> SEQ ID NO 5
<211> LENGTH: 42
<212> TYPE: RNA
<213> ORGANISM: Artificial Sequence
<220> FEATURE:
<223> OTHER INFORMATION: synthetic oligonucleotide

<400> SEQUENCE: 5
gggaacggug ccaguccgaa acggaucguu agagcaucag ua                          42

<210> SEQ ID NO 6
<211> LENGTH: 38
<212> TYPE: RNA
<213> ORGANISM: Artificial Sequence
<220> FEATURE:
<223> OTHER INFORMATION: Artificial oligonucleotides

<400> SEQUENCE: 6
gggucguuag agcaucagua caccaacggu gcgagccc                               38

```
<210> SEQ ID NO 7
<211> LENGTH: 20
<212> TYPE: RNA
<213> ORGANISM: Artificial Sequence
<220> FEATURE:
<223> OTHER INFORMATION: Synthetic Oligonucleotide

<400> SEQUENCE: 7
gggagaauuc aacugccauc                                              20
```

SUBUNIT-SELECTIVE NUCLEIC ACID INHIBITORS OF GLUTAMATE RECEPTORS

CROSS-REFERENCE TO RELATED APPLICATIONS

This application is a U.S. national stage filing under 35 U.S.C. §371 of PCT international application no. PCT/US2011/044206, filed Jul. 15, 2011 and published in English on Apr. 12, 2012 as WO 2012/047355 and claims the priority of U.S. provisional application Ser. No. 61/365,020 filed Jul. 16, 2010; the contents of these applications, are hereby incorporated by reference in their entirety into the present application.

STATEMENT OF RIGHTS UNDER FEDERALLY-SPONSORED RESEARCH

This invention was made with government support under grant W81XWH-04-1-0106 and W81XWH-09-1-0568 awarded by the U.S. Department of Defense. The government has certain rights in the invention.

REFERENCE TO A SEQUENCE LISTING SUBMITTED AS A TEXT FILE

The official copy of the sequence listing is submitted concurrently with the specification as a text file via EFS-Web, in compliance with the American Standard Code for Information Interchange (ASCII), with a file name of 0794123AWO_SequenceListing_ST25.txt, a creation date of Jul. 15, 2011, and a size of 1.77 KB. The sequence listing filed via EFS-Web is part of the specification and is hereby incorporated in its entirety by reference herein.

FIELD OF THE INVENTION

The invention relates to nucleic acid ligands, or aptamers, that bind to AMPA glutamate receptors and inhibit the activity of these receptors. More particularly, the nucleic acid ligands of the present invention selectively bind to a single subunit of the AMPA glutamate receptor.

BACKGROUND OF THE INVENTION

Ion channel glutamate receptors are ligand-gated transmembrane proteins that can be activated by the binding of glutamate, the principal excitatory neurotransmitter in the brain. Ionotropic glutamate receptors (iGluRs) are, therefore, the major excitatory neurotransmitter receptor proteins in the mammalian brain. As such, these receptors play special roles in brain activities, such as memory and learning, and have been implicated in a variety of neurological diseases, such as post-stroke cellular lesion and amyotrophic lateral sclerosis (1, 2).

When glutamate is released from a presynaptic neuron and binds to a postsynaptic glutamate receptor, the receptor rapidly changes its conformation and transiently forms an open ion channel, thus resulting in a change of the postsynaptic membrane potential. A postsynaptic potential of sufficient strength triggers an action potential, which will in turn propagate the initial nerve impulse. The major function of iGluRs is to mediate fast synaptic neurotransmission underlying the basic activities of the brain, for example, memory and learning. Excessive activation of ionotropic glutamate receptors, particularly the α-amino-3-hydroxy-5-methyl-4-isoxazole-propionate (AMPA) subtype, is known to induce calcium-dependent excitotoxicity. Excitotoxicity has been considered as a general mechanism underlying a number of neurodegenerative disorders such as amyotrophic lateral sclerosis (ALS), stroke, Alzheimer's disease and Parkinson's syndrome.

AMPA receptors are one of the three subtypes of glutamate ion channels that also include kainate and N-methyl-D-aspartate (NMDA) subtypes (1, 3-5). AMPA receptors mediate most of fast synaptic neurotransmission in the mammalian central nervous system, and their function and regulation are critical for synaptic plasticity (5, 6). GluA1-4 (previously known as GluR1-4 or GluRA-D) encode four subunits of mammalian AMPA receptors. The primary molecular architecture of AMPA receptor subunits is most likely similar, given the fact that all subunits have ~900 amino acids and share 70% homology of the encoding genes, although the genes are alternatively spliced and edited (1, 3, 4). AMPA receptor subunits are differentially expressed and developmentally regulated. For instance, in embryonic rat brain, GluA2 mRNA is ubiquitous (7). GluA1-3 are expressed in greater proportion in regions such as hippocampus (8), whereas GluA4 is mainly expressed early during development (9, 10). Although GluA1-4 can form homomeric channels individually (11, 12), each subunit has some distinct functional properties. For example, in response to the binding of glutamate, each of the GluA2-4 homomeric receptors opens the channel, with a kinetic rate constant about several-fold larger than GluA1 does, yet all AMPA receptors close their channels with roughly a similar rate (13, 14).

Using inhibitors to dampen the excessive activity of these receptors may serve as a treatment for neurological disorders such as amyotrophic lateral sclerosis (ALS) or Huntington's disease. To date, Riluzole, an inhibitor of presynaptic glutamate release, is the only drug to produce a significant benefit to the survival of ALS patients. The number of glutamate receptor inhibitors currently available is limited and these inhibitors generally show cross activity to other receptors, for example, kainate receptors. The cross activity is not desirable, because the AMPA and kainate receptors have functional differences. Furthermore, the majority of AMPA receptor inhibitors have poor water solubility. In addition, there is a lack of an assay of inhibitor-receptor interactions within the microsecond (µs) to millisecond (ms) time domain. This is because an AMPA receptor opens its channel in the µs time scale and desensitizes within a few ms in the continued presence of glutamate. Consequently, the affinity of all AMPA receptor inhibitors has been determined only with the desensitized receptors. These deficiencies have significantly hampered drug development.

Because proteins are generally dynamic and adapt a specific conformation for function, using molecular agents that bind selectively to a specific protein conformation among its conformational repertoire is thus a powerful means to exert a tighter molecular recognition to more effectively regulate the existing function of that protein, and to even engineer a new protein function. For instance, small chemical compounds have been found to stabilize a conformation for some apoptotic procaspases to induce autoproteolytic activation of these proenzymes. Catalytic antibodies have been created, based on transition-state structural analogs, to accelerate chemical reactions by stabilizing their rate-determining transition states along reaction pathways. Developing inhibitors to control excessive receptor activity has been a long pursued therapeutic strategy for a potential treatment of these neurological disorders and diseases.

Additionally, developing inhibitors to selectively target a single subunit of a multi-subunit protein or receptor family is a worthy effort for the following reasons. First, the role of the single subunit can be uniquely tested in a complex biological background, such as in vivo, leaving other subunits untouched. Such a test can be carried out at any particular time if the target function changes during development. In this scenario, the function of this subunit can be inhibited in a reversible, graded fashion in that the degree of inhibition of the protein function can be manipulated by the amount and the time of exposure when the inhibitor is applied, and such an inhibition can be reversibly relieved when the inhibitor is removed. Second, if the inhibitor is a drug candidate, selectivity is generally a desired property. A drug with higher selectivity may have a higher therapeutic effect when the excessive activity of a single protein subunit to which the drug molecule binds is linked to the pathogenesis of a disease. Third, development of an inhibitor to exclusively differentiate its binding to and inhibition of one subunit can provide valuable insights into the structural and functional differences of the subunit from all other subunits of the same family. As such, the most effective way to probe the structure of a particular subunit and to regulate the function of that subunit may be found.

Given the similarities and differences among various AMPA receptor subunits, it would be useful to develop subunit-selective inhibitors of AMPA receptors. What is needed, therefore, are subunit-selective AMPA glutamate receptor inhibitors that are characterized by a high affinity for its target, preferably in the nanomolar range, specificity targeting a single subunit of a glutamate receptor, excellent water solubility and relevance of its inhibitory properties to the functional forms of the receptor rather than the desensitized receptor forms.

SUMMARY OF THE INVENTION

The present invention provides inhibitors of AMPA-type glutamate ion channels that are useful as biochemical probes for structure-function studies and as potential therapeutic agents for a number of neurological disorders and diseases.

In one aspect, the present invention relates to aptamers that are selective noncompetitive inhibitors of AMPA-type glutamate ion channels; they bind to and selectively inhibit the GluA2Q AMPA receptor subunit without any effect on other AMPA receptor subunits or on kainate or NMDA receptors. Furthermore, the aptamers of the invention preferentially inhibit the closed-channel state of GluA2Q$_{flip}$ with a $K_I$=1.5 μM or by ~15-fold over the open-channel state.

The aptamers of the present invention provide a class of water-soluble, high affinity compounds, that do not inhibit glutamate binding to the AMPA glutamate receptor. In particular, the novel nucleic acid ligands or aptamers of the present invention selectively target the closed-channel conformation of α-amino-3-hydroxy-5-methyl-4-isoxazole propionic acid (AMPA)-subtype glutamate ion channel receptor proteins. The closed-channel conformation of AMPA-subtype glutamate ion channel receptor exists in the time span of microsecond (μs) to a few milliseconds (ms) after glutamate, the endogenous neurotransmitter, binds to the receptor, but before these glutamate-bound receptors turn into the desensitized, closed-channel receptor form.

In one aspect, therefore, the invention relates to isolated nucleic acids consisting essentially of the nucleotide sequence of SEQ ID NO: 1, truncated forms and combinations of truncated forms thereof. The nucleotides of the aptamer may be chemically modified either prior to or after selection or synthesis. In one embodiment, the nucleic acid of the invention is an RNA. Other aptamers of the invention include truncated forms of AF1422, for example, those that have a nucleotide sequence selected from the group consisting of SEQ ID NO.: 2, SEQ ID NO.: 3, SEQ ID NO.: 4, SEQ ID NO.: 5, SEQ ID NO.: 6, and SEQ ID NO.: 7 Inhibition comparable to that seen with untruncated AF1422 can be achieved with truncated forms of AF1422 when aptamers representing complementary regions, (for example, AF44 and AF42) of AF1422 are combined.

In another aspect, the invention relates to a method of modulating the activity of a glutamate receptor comprising contacting a glutamate receptor with a nucleic acid inhibitor of the invention that selectively binds a single subunit of the receptor and has been shown to have an inhibitory effect.

In another related aspect, the invention relates to a DNA that encodes an aptamer capable of inhibiting AMPA glutamate receptors.

In yet another aspect, the invention relates to a pharmaceutical composition comprising an AMPA glutamate receptor inhibitor of the invention and, optionally, a pharmaceutically acceptable carrier.

In a related aspect, the invention relates to a method of treatment for a disease or condition characterized by excessive activation of ionotropic glutamate receptors, the method comprising administering to the subject in need of such treatment, a therapeutically effective amount of the nucleic acid inhibitor of the invention. These and other objects, features and advantages of this invention will become apparent from the following detailed description of the various aspects of the invention taken in conjunction with the accompanying drawings.

$$Y = \frac{B_{max} \times [Hot]}{[Hot] + [Cold] + K_d} + NSB \quad (eq. 1)$$

Figure 11:
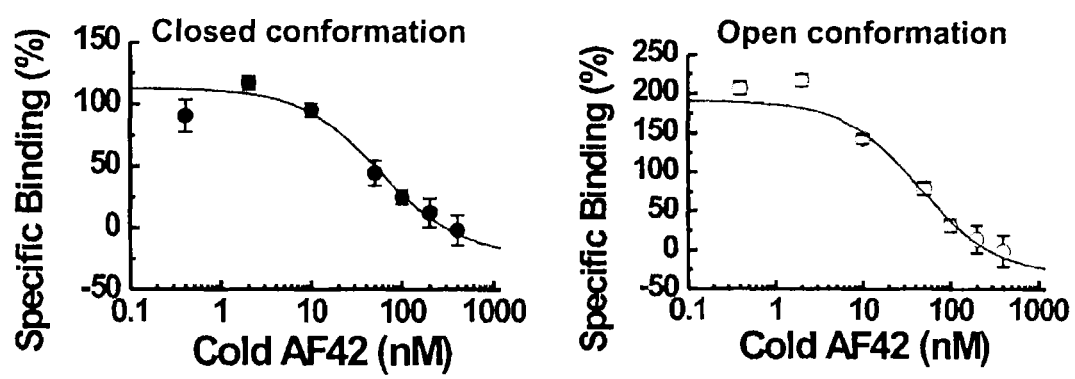

FIG. 11 shows the results of homologous competition binding assay of AF42 (cold and hot) to GluA2Q$_{flip}$ receptor, in which the binding constant, $K_d$, was calculated based on triplicate data sets, using Equation 1, was found to be 57±21 nM for the closed-channel conformation (left panel) and 44±11 nM for the open-channel (right panel) conformation of GluA2Q$_{flip}$, respectively.

Figure 12:
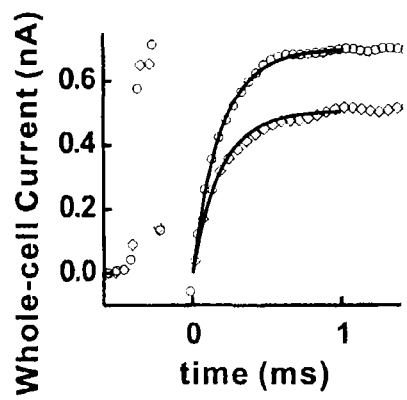
Figure 12:
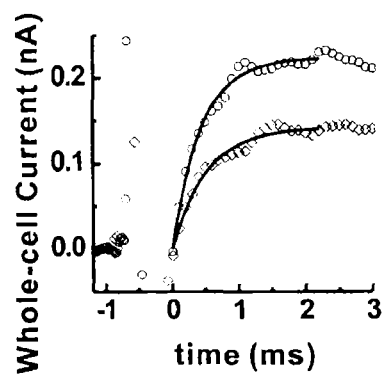

FIG. 12 shows the results of laser-pulse photolysis measurement of the effect of AF44/AF42 on the channel-opening rate of GluA2Q$_{flip}$. At 300 µM photolytically released glutamate concentration (left panel), $k_{obs}$ was 4975±173 s$^{-1}$ for the control (open circle), but was 4273±146 s$^{-1}$ in the presence of 1 µM AF44/AF42 (open diamond). The first order rate constants were calculated as the best fit (see the solid line in both traces) by Equation 3. The current amplitude in the absence and presence of aptamer was 0.70 nA and 0.51 nA, respectively. At 100 µM photolytically released glutamate concentration, $k_{obs}$, which reflected $k_{cl}$, was similarly estimated to be 2297±36 s$^{-1}$ and the current amplitude was 0.23 nA in the absence of AF44/AF42 (open circle). In the presence of 1 µM AF44/AF42 (open diamond), $k_{obs}$ was found to be 2223±25 s$^{-1}$ and the current amplitude was 0.15 nA. The initial spikes prior to the current rise were discharge signal from the laser flash.

Figure 13:
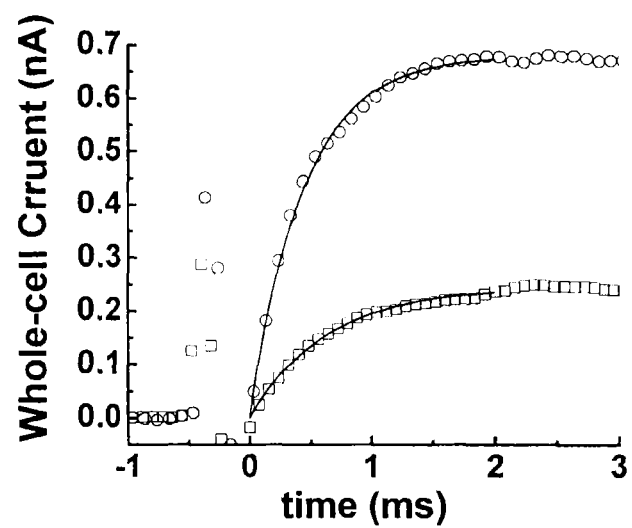

FIG. 13 shows the results of laser-pulse photolysis measurement to show that only at a high concentration of AF44/AF22, the $k_{obs}$, which reflects $k_{cl}$ for the open-channel conformation, can be inhibited. Specifically, at 100 µM photolytically released glutamate concentration, $k_{obs}$ was determined to be 2204±43 s$^{-1}$ and the current amplitude through the GluA2Q$_{flip}$ channels was 0.68 nA in the absence of AF44/AF42 (upper trace). In the presence of 3 µM AF44/AF42 (lower trace), $k_{obs}$ was found to be 1490±10 s$^{-1}$ and the amplitude was 0.25 nA. This result shows that the open-channel conformation is inhibited by AF44/AF42, albeit weakly.

Figure 14:
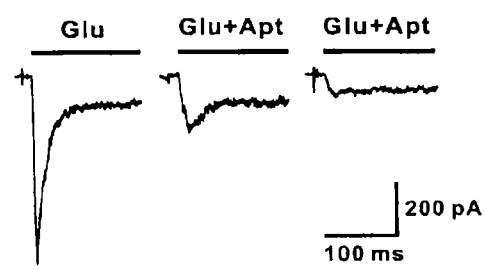
Figure 14:
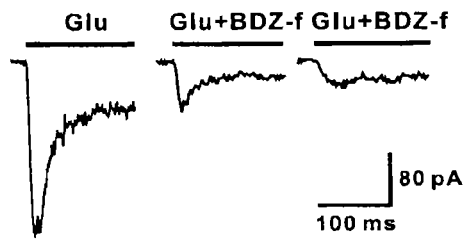

FIG. 14 shows inhibition of the whole-cell current response from the GluA2Q$_{flip}$ channels at very high concentrations of AF44/AF42 (A) and BDZ-f (B), where the non-desensitizing phase of the receptor response was uninhibited by either aptamer or BDZ-f, as shown by the trace in the right panel in both (A) and (B). All of the traces are drawn to scale. The receptor response was evoked by 0.1 mM of glutamate in both (A) and (B). In (A), the AF44/AF42 used was 6.25 µM (middle panel) and 12.5 µM (right panel); in (B), the concentration of BDZ-f used was 10 µM (middle panel) and 20 µM (right panel).

FIG. 15 is a table showing the nucleotide sequences of some of the aptamers of the invention.

DETAILED DESCRIPTION OF THE INVENTION

All patents, publications, applications and other references cited herein are hereby incorporated by reference into the present application. Methodology used in developing the present invention are well known to those of skill in the art and are described, for example, in Sambrook et al., 2001, *Molecular Cloning: A Laboratory Manual*, Third Edition, Cold Spring Harbor Laboratory Press, Cold Spring Harbor, N.Y.; *DNA Cloning: A Practical Approach*, Volumes I and II, 1985 (D. N. Glover ed.); *Oligonucleotide Synthesis*, 1984 (M. L. Gait ed.), the contents of which are hereby incorporated by reference. In the description that follows, certain conventions will be followed as regards the usage of terminology.

The following abbreviations are used throughout the specification:

AMPA α-amino-3-hydroxy-5-methyl-4-isoxazole propionic acid
NMDA N-methyl-D-aspartate
BDZ-f 1-(4-aminophenyl)-3-methylcarbamoyl-4-methyl-7,8-methylenedioxy-3,4-dihydro-5H-2,3-benzodiazepine
NBQX 6-nitro-7-sulfamoyl-benzo[f]quinoxaline-2,3-dione
Caged glutamate γ-O-(α-carboxy-2-nitrobenzyl) glutamate The term "aptamer" refers to a nucleic acid or oligonucleotide molecule that binds to a specific molecular target such as a protein receptor. Aptamers with the desired binding characteristics are identified through an in vitro evolutionary process known as SELEX (Systematic Evolution of Ligands by EXponential Enrichment), which selects target-specific aptamer sequences from large combinatorial libraries of single stranded oligonucleotide templates comprising randomized sequences. The aptamers of the invention may be synthesized by any method known to those in the chemical arts, including recombinant techniques. Aptamer compositions may be double-stranded or single-stranded, and may include deoxyribonucleotides, ribonucleotides, nucleotide derivatives, or other nucleotide-like molecules. The nucleotide components of an aptamer may include modified or non-natural nucleotides, for example nucleotides that have modified sugar groups (e.g., the 2'-OH group of a ribonucleotide may be replaced by 2'-F or 2'—NH$_2$), which may improve a desired property, e.g., resistance to nucleases or longer lifetime in blood. Aptamers may also be conjugated to other molecules, e.g., a high molecular weight carrier to slow clearance of the aptamer from the circulatory system. Aptamers may be specifically cross-linked to their cognate ligands, e.g., by photo-activation of a cross-linker. [Brody, E. N. and L. Gold (2000) J. Biotechnol. 74:5-13.].

The term "nucleic acids," or "oligonucleotides," as used herein, refers to a polymer of nucleotides. Typically, a nucleic acid comprises at least three nucleotides. The polymer may include natural nucleosides (i.e., adenosine, thymidine, guanosine, cytidine, uridine, deoxyadenosine, deoxythymidine, deoxyguanosine, and deoxycytidine) or modified nucleosides. Modifications include, but are not limited to, those which provide other chemical groups that incorporate additional charge, polarizability, hydrogen bonding, electrostatic interaction, and fluxionality to the nucleic acid ligand bases or to the nucleic acid ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil, backbone modifications, methylations, unusual base-pairing combinations such as the isobases isocytidine and isoguanidine and the like. Modifications can also include 3' and 5' modifications such as capping. Examples of modified nucleotides include, for example, base modified nucleoside (e.g., aracytidine, inosine, isoguanosine, nebularine, pseudouridine, 2,6-diaminopurine, 2-aminopurine, 2-thiothymidine, 3-deaza-5-azacytidine, 2'-deoxyuridine, 3-nitorpyrrole, 4-methylindole, 4-thiouridine, 4-thiothymidine, 2-aminoadenosine, 2-thiothymidine, 2-thiouridine, 5-bromocytidine, 5-iodouridine, inosine, 6-azauridine, 6-chloropurine, 7-deazaadenosine, 7-deazaguanosine, 8-azaadenosine, 8-azidoadenosine, benzimidazole, M1-methyladenosine, pyrrolo-pyrimidine, 2-amino-6-chloropurine, 3-methyl adenosine, 5-propynylcytidine, 5-propynyluridine, 5-bromouridine, 5-fluorouridine, 5-methylcytidine, 7-deazaadenosine, 7-deazaguanosine, 8-oxoadenosine, 8-oxoguanosine, O(6)-methylguanine, and 2-thiocytidine), chemically or biologically modified bases (e.g., methylated bases), modified sugars (e.g., 2'-fluororibose, 2'-aminoribose, 2'-azidoribose, 2'-O-methylribose, L-enantiomeric nucleosides arabinose, and hexose), modified phosphate groups (e.g., phosphorothioates and 5'-N-phosphoramidite linkages), and combinations thereof. Natural and modified nucleotide monomers for the chemical synthesis of nucleic acids are readily available (e.g. see the following urls: trilinkbiotech, appliedbiosystems, biogenex or syngendna).

As used herein, a "nucleic acid ligand" is a non-naturally occurring nucleic acid that binds selectively to a target, generally a protein. The nucleic acid that forms the nucleic acid ligand may be composed of naturally occurring nucleosides, modified nucleosides, naturally occurring nucleosides with hydrocarbon linkers (e.g., an alkylene) or a polyether linker (e.g., a PEG linker) inserted between one or more nucleosides, modified nucleosides with hydrocarbon or PEG linkers inserted between one or more nucleosides, or a combination of thereof. Nucleotides or modified nucleotides of the nucleic acid ligand can be replaced with a hydrocarbon linker or a polyether linker provided that the binding affinity and selectivity of the nucleic acid ligand is not substantially reduced by the substitution. Generally, the target molecule of a nucleic acid ligand is a three dimensional chemical structure to which the nucleic acid ligand binds. However, the nucleic acid ligand is not simply a linear complementary sequence of a nucleic acid target, but may include regions that bind via complementary Watson-Crick base pairing interrupted by other structures such as hairpin loops to adopt a secondary structure. Generally, the nucleic acid ligand binds to a cell surface target that is associated with a specific disease state. A preferred target is a protein on the surface of a cell, such as a cell surface receptor, or an ion channel. More preferably, the target is a glutamate receptor.

The traditional approach to find chemical inhibitors is synthetic chemistry, which produces small molecule inhibitors, the most common type of molecular agents and drug candidates (15-17). In fact, a large number of small molecule inhibitors that target AMPA receptors have been synthesized (18-20). To date, no inhibitor is known to be capable of selectively inhibiting a single AMPA receptor subunit. Therefore, from the outset, no structural template was available for either a synthetic or a natural product inhibitor that might be most obvious to modify and/or improve upon in order to generate a subunit-selective inhibitor.

The approach that was taken in developing the inhibitor of the present invention was based on an in vitro evolution for isolating RNA inhibitors or aptamers from an RNA library (21, 22). This approach relies on reverse transcription-polymerase chain reaction (PCR) to "breed" desired RNA molecules by exponential enrichment of their sequences over background, through multiple iterative cycles, against a specific target protein or receptor. The useful RNA molecules are selected because they are the best fits to the protein target based on geometrical complementarity. Therefore, this approach does not require prior knowledge of the structure of the protein target, nor the existence of any lead compounds (23).

Aptamers were identified that would selectively inhibit the GluA2 AMPA receptor subunit. This subunit was chosen because GluA2 controls key functional properties of heteromeric AMPA receptors, such as $Ca^{2+}$ permeability, single channel conductance and rectification (24, 25). These properties of GluA2 are attributed to Arg607, a residue at the glutamine (Q)/arginine (R) site introduced into the pore loop by RNA editing (24, 25). The Q/R editing is exclusive to GluA2 in AMPA receptors, and the editing is extremely efficient (i.e., >99% of GluA2 in adult brain is in the edited, R isoform) (26). Editing defect in GluA2, however, leads to generation of the highly $Ca^{2+}$ permeable Q isoform through which excessive $Ca^{2+}$ ions enter the cell. Consequently, intracellular calcium overload causes cell death, which underlines various neurological disorders, such as stroke (27) and amyotrophic lateral sclerosis (ALS) (28). Thus, GluA2 subunit-selective aptamers are potential drug candidates. These aptamers could be also used as structural probes.

To find GluA2-selective aptamers, the closed-channel receptor conformation was chosen as the target of the selection, rather than the open-channel or a mixture of the closed- and the open-channel conformations (for the purpose of this work, the closed-channel conformation is defined as the unliganded, resting form of the receptor. The choice of this conformation was based on an earlier hypothesis that the closed-channel conformation is more flexible or more modifiable in the context of inhibitor binding/inhibition (29). Therefore, the closed-channel conformation would be a better structural scaffold for geometrical complementarity selection (30). As such, an RNA aptamer, selected to uniquely recognize one conformation of a subunit, is not expected to bind avidly to either other receptor subunits or even other conformations of the same subunit due to incorrect or imperfect molecular recognition, thereby producing subunit discrimination and selectivity.

To maximize the chance of finding subunit-selective inhibitors, competitive inhibitor types were not selected, despite the fact that there is abundant, structural information available for competitive inhibitors and the agonist binding sites (31-35). Instead, noncompetitive inhibitors were selected. Because noncompetitive inhibitors bind to regulatory sites, distinct from the site to which agonist binds, they are generally considered more selective or less promiscuous in differentiating isoforms.

By applying these mechanism-based design principles, together with the use of an in vitro evolution approach, an initial aptamer, AF1422, was isolated that not only has a nanomolar affinity but is exclusively selective to the GluA2 AMPA receptor subunit.

In one embodiment, therefore, the present invention encompasses an aptamer consisting essentially of the nucleotide sequence of SEQ ID NO: 1. Truncated forms of the aptamer that retain the inhibitory activity of AF1422 are also encompassed by the invention as are combinations of truncated forms that demonstrate inhibitory activity.

Nucleic acid ligands of the invention may be prepared by any method known to those of skill in the art, including chemical synthesis, isolation from a nucleic acid library or by recombinant technology. In one embodiment, the method of preparing a nucleic acid ligand of the invention begins by identifying nucleic acid ligands from a candidate mixture of nucleic acids by Systemic Evolution of Ligands by Exponential Enrichment (SELEX), or a variation thereof, which is a commonly used method of identifying nucleic acid ligands that bind to a target from a candidate mixture of nucleic acids.

The SELEX process for obtaining nucleic acid ligands is described in U.S. Pat. No. 5,567,588, (the contents of which are hereby incorporated by reference) and may include the following steps:
1) A candidate mixture of nucleic acids of differing sequence, for example, a combinatorial RNA library, is prepared.
2) The candidate mixture is contacted with a selected target under conditions favorable for binding between the target and members of the candidate mixture. Under these circumstances, the interaction between the target and the nucleic acids of the candidate mixture can be considered as forming nucleic acid-target pairs between the target and the nucleic acids having the strongest affinity for the target.
3) The nucleic acids with the highest affinity for the target are partitioned from those nucleic acids with lesser affinity to the target using known ligands for the receptor. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 0.1%-10%) is retained during partitioning.
4) Those nucleic acids selected during partitioning as having the relatively higher affinity to the target are then amplified to create a new candidate mixture that is enriched in nucleic acids having a relatively higher affinity for the target.
5) By repeating the partitioning and amplifying steps above, the newly formed candidate mixture contains fewer and fewer unique sequences, and the average degree of affinity of the nucleic acid mixture to the target will generally increase. Taken to its extreme, the SELEX process will yield a candidate mixture containing one or a small number of unique nucleic acids representing those nucleic acids from the original candidate mixture having the highest affinity to the target molecule.

To elucidate the channel-opening kinetic mechanism of the homomeric channel with and without aptamer ligand, a rapid kinetic technique that has a µs time resolution, namely laser pulse photolysis of caged glutamate, was used. The channel opening rate constant, the channel closing rate constant or the lifetime of the channel, and the dissociation equilibrium constant for glutamate were determined. Thus, by this methodology, the mechanism of action, the affinity, and selectivity of each aptamer on the functional forms of each receptor subunit was characterized.

The present invention provides novel nucleic acids that inhibit the activity of ionotropic glutamate receptors, and in particular, provide subunit-selective, non-competitive inhibition of the closed channel conformation of the α-amino-3-hydroxy-5-methyl-4-isoxazole-propionate (AMPA) subtype of glutamate receptor. A modified SELEX method was used to identify the nucleic acid ligands disclosed herein. Once a glutamate receptor-specific aptamer was identified, the aptamer's ability to inhibit glutamate function was evaluated. By providing a cell that has been transfected to overexpress the glutamate receptor and measuring glutamate-induced whole-cell current in a single cell in the presence and absence of the nucleic acid identified by SELEX, a comparison of the measurement of whole cell current in the presence and absence of nucleic acid was informative of the aptamer's potential as a glutamate receptor inhibitor. A decrease in the whole-cell current in the cell in the presence of nucleic acid as compared to the whole-cell current in the absence of nucleic acid indicated that the nucleic acid inhibits glutamate receptor function.

To arrive at the novel inhibitors of the present invention, therefore, a novel combination of two approaches was used, namely an in vitro iterative procedure, SELEX, to select the aptamers of the invention from a combinatorial RNA library and a laser-pulse photolysis technique that has a microsecond (µs) time resolution to screen the aptamers against a functional (i.e., non-desensitized) form of the glutamate receptor.

To find inhibitors selectively targeting the closed-channel conformation of AMPA receptors, SELEX, was used to identify potential RNA inhibitors or aptamers from an RNA library that contained ~$10^{15}$ randomized sequences ((21, 22)). This approach mimics how immune system works by generating and screening a tremendous number of RNAs to identify a desired RNA molecule(s) with a defined property without pre-existing templates—a concept and practice different from conventional organic synthesis to produce small molecule inhibitors. RNA aptamers can fold into potentially useful three-dimensional structures, and can be evolved using SELEX to recognize virtually any target molecules as well as perform desired functions with high affinity and selectivity not found in nature ((23)). Specifically, the GluA2Q$_{flip}$ AMPA receptor was used as the SELEX target, because GluA2 is considered a key subunit that mediates excitotoxicity ((36)), and the unedited or the Q isoform (i.e., glutamine at the glutamine/arginine or Q/R editing site) is calcium-permeable, whereas the R isoform is not ((24)). Abnormal expression of the Q isoform of GluA2 is linked to neurological disorders such as ALS ((28)).

Through multiple rounds of SELEX, four enriched RNA sequences were identified from 92 clones randomly chosen from rounds 12 and 14. An enriched sequence was one with at least two copies in the entire sequence pool of 92 clones.

Figure 2:
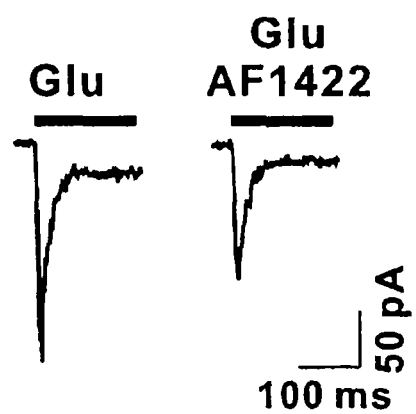
FIG. 2 shows representative traces of the whole-cell current response of GluA2Q$_{flip}$ to 100 μM glutamate in the absence (left panel) and presence (right panel) of 104 of an aptamer of the invention, AF1422.
Figure 3:
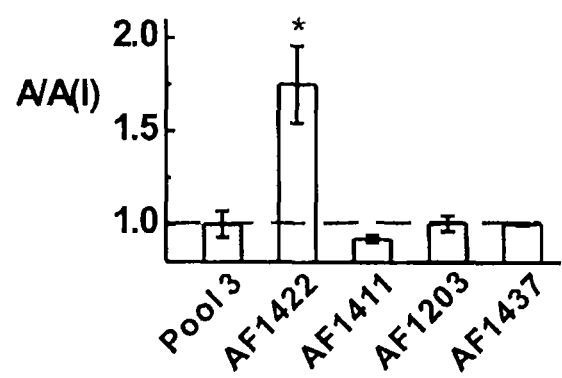
FIG. 3 shows the results of the whole-cell current recording assay in which AF1422 selectively inhibited the closed-channel conformation of the AMPA receptor.

The putative inhibitory property of the four sequences was then functionally tested by the use of whole-cell current recording with GluA2Q$_{flip}$ expressed in HEK-293 cells. Representative traces of the whole-cell current response of GluA2Q$_{flip}$ to 100 µM glutamate in the absence (left panel) and the presence (right panel) of 1 µM of aptamer AF1422 are shown in FIG. 2. The current was recorded at −60 mV, pH 7.4 and 22° C. with the same HEK-293 cells expressing GluA2Q$_{flip}$ that were used for selection. Based on the whole-cell recording results or the ratio of the current amplitudes in the absence and presence of an aptamer, A/A(I), AF1422, the most enriched sequence, was one of the most potent inhibitors (FIG. 3). A further test of AF1422 at the same aptamer concentration but with increasing glutamate concentrations showed that AF1422 inhibited the closed-channel, preferentially over the open-channel, conformation of GluA2Q$_{flip}$.

Next AF1422 was systematically truncated to identify the minimal, yet functional sequence. From the secondary structures predicted by Mfold program, shorter versions of AF1422 (FIG. 4) were constructed and then functionally tested.

Figure 4:
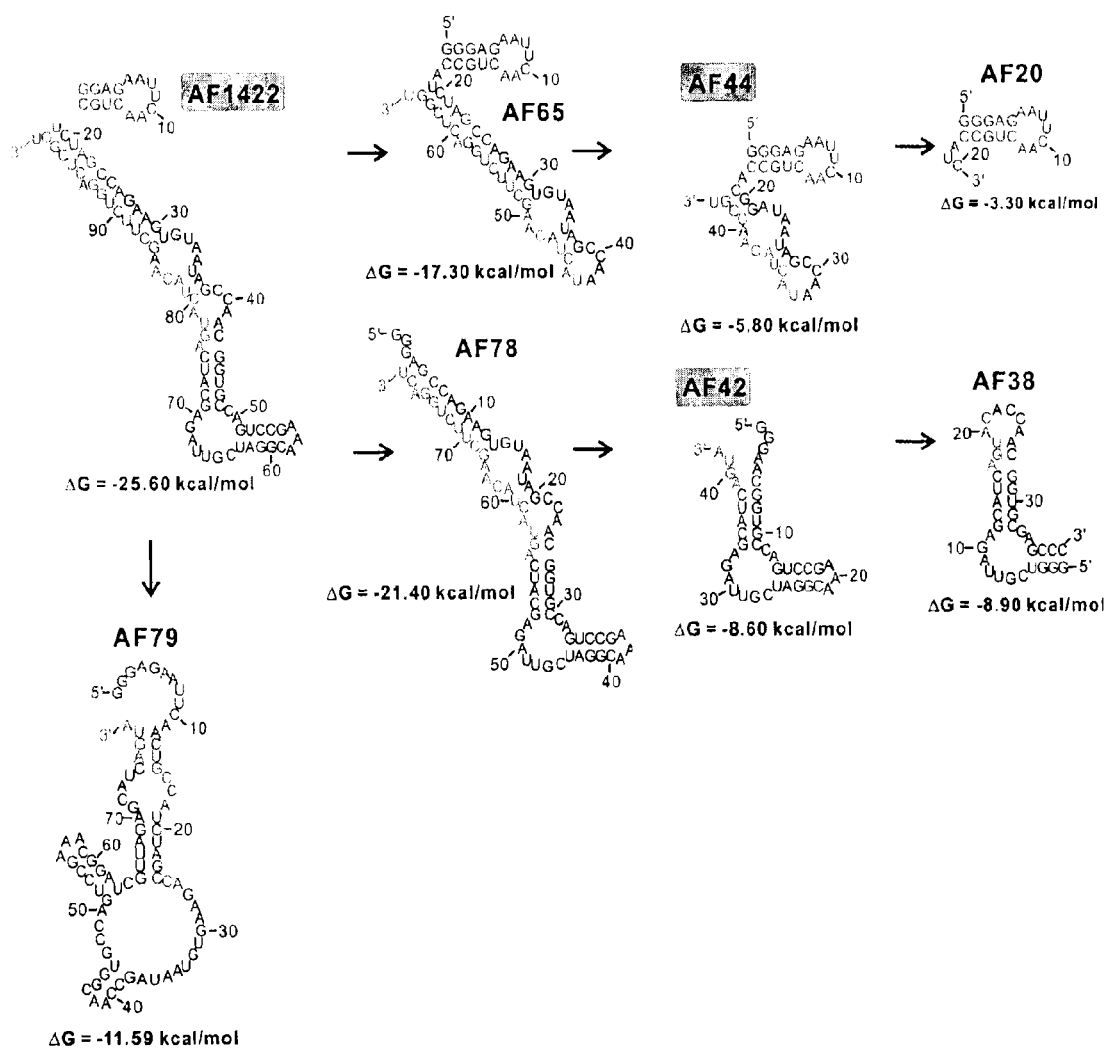
FIG. 4 shows secondary structures of some embodiments of the aptamers of the invention based on Mfold model predictions. AF1422 (SEQ ID NO: 1) was truncated to determine a minimal, functional sequence. Truncated sequences AF78 (SEQ ID NO: 3), AF79 (SEQ ID NO: 8), AF65 (SEQ ID NO: 2), AF44 (SEQ ID NO: 4), AF42 (SEQ ID NO: 5), AF38 (SEQ ID NO: 6), AF20 (SEQ ID NO: 7) are shown.
Figure 5:
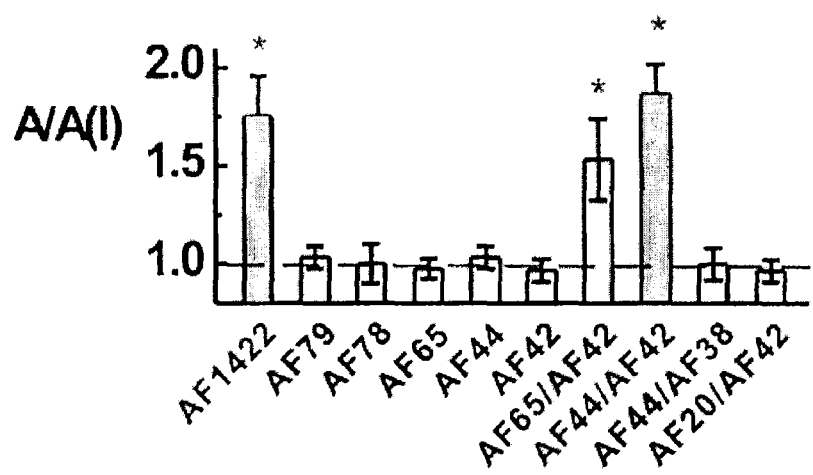
FIG. 5 shows the results of a whole-cell current recording assay in which A/A(I) was determined for various truncated forms of AF1422. While many of the truncated forms did not show activity, inhibition could be restored by some combinations of the truncated forms.

To create shorter pieces of RNAs (FIG. 4), we preserved the predicted secondary structures that were thought to be important. For example, AF78 was constructed to test whether the stem-loop structure of AF1422, comprised of the initial 20 or so nucleotides at the 5' constant region, played any functional role. The fact that AF78 turned out to be non-inhibitory suggested that this region was essential for inhibition by AF1422. However, AF20, which contained only this stem loop, was not sufficient to act either alone as an inhibitor or together with AF42 as an inhibitory pair (FIG. 4). In contrast, AF44, which carries this stem-loop module, was capable of acting with AF42 as an inhibitory pair (FIG. 5). Furthermore, based on the functional combination of AF44 and AF42, a removal of the terminal loop from the AF42 resulting AF38 led to a total loss of function, suggesting that this terminal loop was essential.

To create AF44, we modified the projected secondary structure of AF1422 (FIG. 2A) in the following way. First, the stem formed from U19/G99 to U31/G86 was significantly shortened by retaining only three-GC base pairs, i.e., C20/G98, G27/C90 and G30/C87. Second, to maintain the two central loops as in AF1422 (FIG. 4), nucleotide G22 was replaced with A22, (note that G22 is numbered as the nucleotide position in the truncated sequence as in FIG. S2B; in the wild-type AF1422 sequence, it corresponds to G32. Without this replacement, the shorter sequence carrying G22 (i.e., AF44 wild-type) showed no activity at all with GluA2 receptor channels when it combined with AF42 (data not shown). This was because the wild-type sequence in AF44(G22) could no longer fold into the same secondary structure as in the central loop of AF1422. Yet, AF44(A22) was projected to fold into a structure resembling the central loop of AF1422 with a shortened stem.

By monitoring the A/A(I) value, the inhibitory function of the shorter RNA pieces was tested one at a time. For aptamers less than 80 nucleotides, none worked alone as an inhibitor (FIG. 5). The shortest, functional aptamer equivalent of AF1422 turned out to be a pair of aptamers, i.e., truncated forms of AF1422: AF44 and AF42 (AF44 and AF42 represent a 44-nucleotide (nt) RNA and a 42-nt RNA molecules respectively). In other words, the use of either AF44 or AF42 alone did not render any inhibition; yet, an equal molar mixture of AF44 and AF42 reproduced an inhibition as full as AF1422 (shown in FIG. 5). Taken together, therefore, AF44 and AF42 are examples of a functional inhibitor aptamer pair and were used for all the subsequent studies below (for convenience, AF44(A22) was simply termed AF44 in this work).

Subunit Selectivity of AF44/AF42

Figure 8:
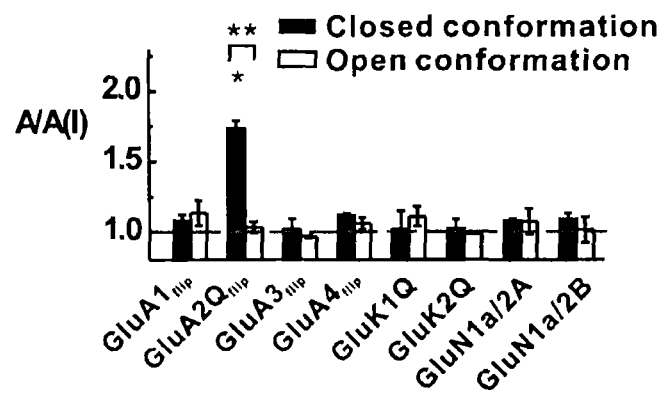
FIGS. 8A and 8B are graphs showing the results of whole-cell current recording assay; 8A shows that AF44/AF42 selectively inhibited the closed-channel conformation of GluA2Q$_{flip}$ and did not affect any other channels as shown. In 8B BDZ-f selectivity for GluA subunits was similarly determined.
Figure 8:
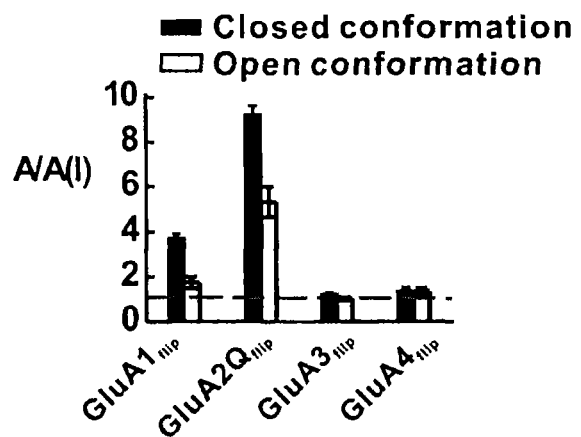

The subunit selectivity of AF44/AF42 was assessed with individual subunits of AMPA, kainate and NMDA receptors expressed in HEK-293 cells, and was represented by A/A(I) value collected from whole-cell recording (FIG. 8A). The selectivity was further determined at two glutamate concentrations, representing the closed-channel and open-channel conformations (see the solid and hollow columns in FIG. 8A). We found that AF44/AF42 did not affect the rest of AMPA receptor subunits, i.e., GluA1, 3 and 4. Furthermore, AF44/AF42 did not affect either kainate channels (i.e., GluK1 and GluK2, the two kainate receptor subunits) or NMDA channels (i.e., GluN1a/2A and GluN1a/2B, the two NMDA receptor channels) (FIG. 8A). It should be mentioned that GluN1a/2A and GluN1a/2B are two dominant NMDA receptor complexes in vivo (37) and neither GluN1a nor GluN2A or GluN2B can form a functional channel by itself (38). These results thus demonstrated that AF44/AF42 is an inhibitor pair that possesses a unique selectivity towards GluA2 but without any unwanted activity on any other subunits of the glutamate ion channel receptor family. These properties are expected because of our design strategy. In contrast, BDZ-f, the chemical compound that we used in the selection of AF1422 inhibited not only GluA2Q$_{flip}$ but also GluA1$_{flip}$ (FIG. 8B). Thus, AF44/AF42 is a better inhibitor in terms of subunit selectivity.

AF44/AF42 is More Potent and Selective to the Flip than the Flop Isoform of GluA2Q Alternative splicing in AMPA receptors generates two variants, i.e., flip and flop (39). The flip/flop sequence cassette is part of the extracellular ligand binding domain, and the C-terminus of this sequence cassette precedes the last transmembrane domain. The flip and flop variants of an AMPA receptor subunit generally have different kinetic properties. The flop variants of AMPA receptor subunits, with the exception of GluA1, have similar $k_{op}$, yet different $k_{cl}$ values (13, 40); they desensitize at least three times faster, but recover more slowly from desensitization than the flip counterparts (11, 13, 40, 41).

Figure 6:
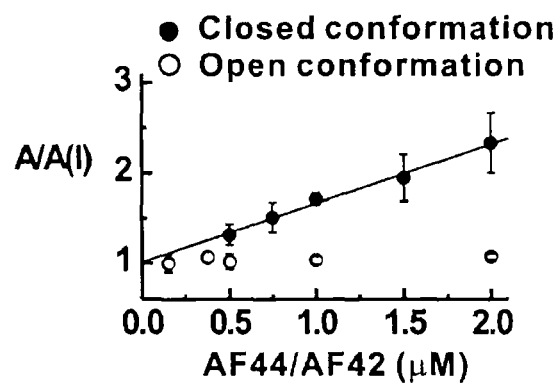
FIG. 6A shows the results of a whole-cell current recording assay in which AF44/AF42 inhibited the closed-channel, but not the open-channel, conformation of GluA2Q$_{flip}$ for the aptamer concentrations shown.
FIG. 6B shows the whole-cell current response to 3 mM glutamate in the absence (left panel) and presence of 6.25 μM AF44/AF42. The reduction of current amplitude at this aptamer concentration is approximately 20%.
Figure 6:
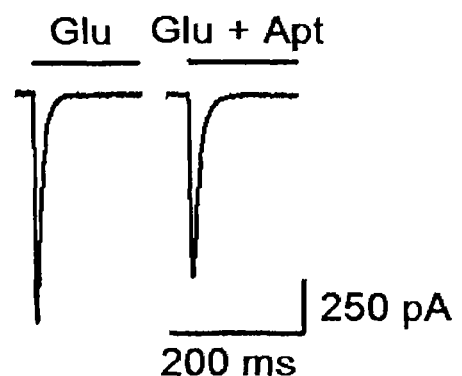
Figure 7:
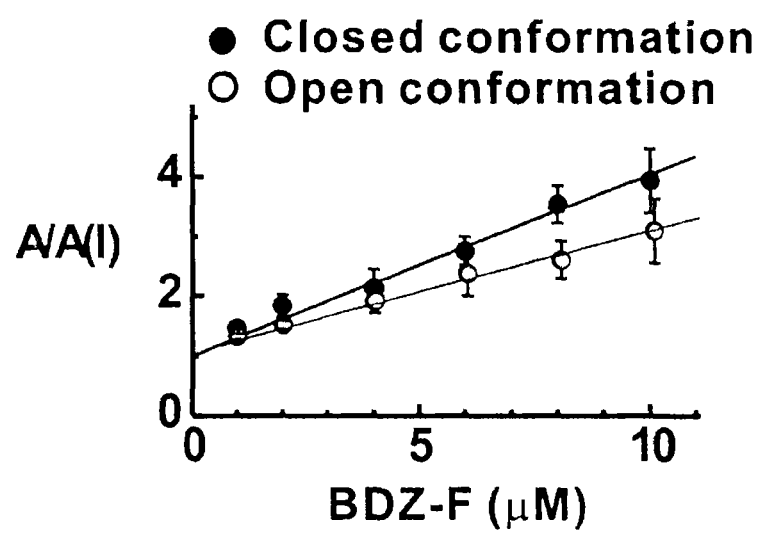
FIG. 7 shows the results of a whole-cell current recording assay in which $K_I$ for BDZ-f was determined to be 3.8±0.4 µM for the closed-channel conformation and 5.4±0.8 µM for the open-channel conformation, respectively.
Figure 9:
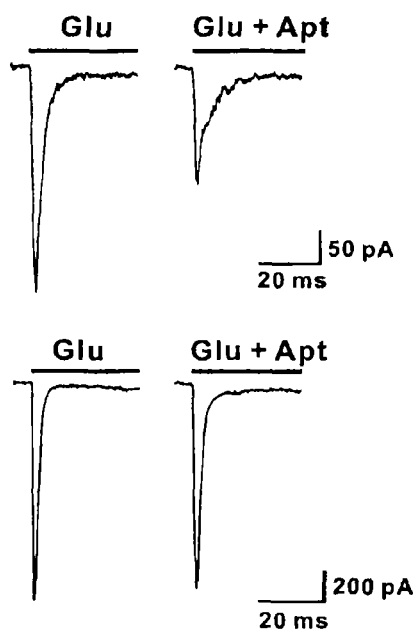
FIG. 9 shows whole-cell current response of GluA2Q$_{flop}$ expressed in HEK-293 cells. The left panel (top) shows the whole-cell current response to 100 µM glutamate keeping the closed-channel conformation, whereas the right panel (top) is the whole-cell current to the same glutamate concentration in the presence of 6.25 µM AF44/AF42. The inhibition of the open-channel conformation of GluA2Q$_{flop}$ by AF44/AF42 was assayed at 3 mM glutamate. Shown are two representative whole-cell current traces in the absence (bottom left panel) and presence (bottom right panel) of 6.25 µM AF44/AF42.

Because of the difference in these properties for the flip and flop variants of GluA2Q, we tested if AF44/AF42 differentially inhibited the flip and flop. Indeed, like the flip variant, AF44/AF42 preferred to inhibit the closed-channel state of GluA2Q$_{flop}$, but with a significantly weaker potency (FIG. 9). The comparison of this result (FIG. 9) with that of the same experiment but with the flip variant (FIGS. 6A and 6B) suggested that AF44/AF42 preferentially inhibited flip over the flop variant of GluA2Q.

Mechanism of Inhibition of AF44/AF42: Homologous Competition Binding Studies

Figure 10:
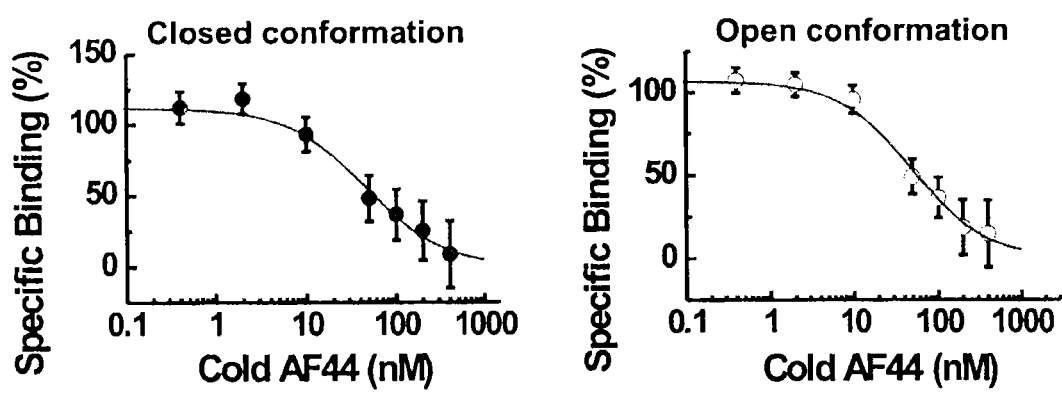
FIG. 10 shows the results of homologous competition binding assay of AF44 (cold and hot) to GluA2Q$_{flip}$ receptor, in which the binding constant, $K_d$, was calculated based on triplicate data sets, using Equation 1, to be 44±18 nM for the unliganded, closed-channel conformation (left panel) and 48±13 nM for the open-channel (right panel) conformation of GluA2Q$_{flip}$, respectively.

The fact that AF44/AF42 inhibited both the closed-channel and the open-channel conformations of GluA2Q$_{flip}$ observed in the amplitude measurements (FIGS. 6A and 6B), although the inhibition of the latter was considerably less potent, was consistent with a noncompetitive mechanism. If this mechanism was indeed operative, AF44/AF42 would be expected to bind to a noncompetitive site, and such a site would be distinct from the glutamate binding site and would be accessible through both the closed-channel and the open-channel conformations. In fact, in a homologous competition binding experiment (42) in which the non-radiolabeled aptamer (or cold aptamer) was used to compete against the same, but radiolabeled, aptamer (or hot aptamer), AF44 bound to not only the closed-channel conformation (i.e., the unliganded, closed-channel receptor form) but also the open-channel conformation (FIG. 10). Specifically, AF44 bound to the two different receptor conformations with equal affinity, i.e., $K_d$=44±18 nM (FIG. 10 left panel, closed-channel conformation) and $K_d$=48±13 nM (FIG. 10 right panel, open-channel conformation), respectively. Likewise, AF42 was found to bind to both the closed-channel conformation ($K_d$=57±21 nM; FIG. 11, left panel) and the open-channel conformation ($K_d$=44±11 nM; FIG. 11 right panel), respectively. The binding results were consistent with noncompetitive sites, because these sites were supposed to be accessible through both the closed- and the open-channel conformations. The fact that AF44 or AF42 alone did not lead to any inhibition and yet each could bind the receptor further suggested that AF44 and AF42 bound to two different sites (FIGS. 10 and 11). These sites were noncompetitive type because binding to the receptor by either AF44 or AF42 or the full length AF1422 was unaffected in the presence of NBQX, a classic competitive inhibitor.

Mechanism of Action of AF44/AF42: a Laser-Pulse Photolysis Measurement of the Effect of AF44/AF42 on the Channel-Opening Rate of $GluA2Q_{flip}$ Using a laser-pulse photolysis technique with ~60 microsecond time resolution (43), we further characterized the mechanism of inhibition of AF44/AF42 by measuring its effect on both $k_{cl}$ and $k_{op}$ of $GluA2Q_{flip}$ (29, 44) (FIG. 12). Specifically in this study, $k_{cl}$ and $k_{op}$ of $GluA2Q_{flip}$ were separately determined at 100 µM and 300 µM glutamate photolytically released by the laser-pulse photolysis of caged glutamate (see the rate equations and quantitative treatment of the kinetic data in Experimental Procedures). The laser-pulse photolysis experiment also permitted us to follow simultaneously both the rate of channel opening and the current amplitude at a given glutamate concentration prior to channel desensitization (29) (FIG. 12).

At 1 µM aptamer concentration and at 300 µM glutamate concentration, AF44/AF42 inhibited $k_{op}$ as compared to the control (FIG. 12 left panel). This was expected because $k_{op}$ reflected the closed-channel conformation and thus the appearance of an inhibitory effect by the aptamer was consistent with the notion that AF44/AF42 inhibited the closed-channel state.

However, at the same aptamer concentration (i.e., AF44/AF42 of 1 µM) but at 100 µM photolytically released glutamate) where $k_{cl}$ was measured (29, 44), AF44/AF42 did not show an inhibition of $k_{cl}$, although it inhibited the current amplitude (FIG. 12, right panel). Only at a higher concentration of aptamer was the inhibition of $k_{cl}$ observed, along with further reduction of amplitude. These results demonstrated that AF44/AF42 had a stronger inhibition towards the close-channel conformation than the open-channel conformation. This conclusion was again consistent with the results described earlier. It should be noted that at a low glutamate concentration (i.e., 100 µM photolytically released glutamate) where $k_{cl}$ was measured (29, 44), the fact that AF44/AF42 inhibited the current amplitude at a low aptamer concentration but without inhibiting $k_{cl}$ was plausible because the macroscopic amplitude observed at a low glutamate concentration (i.e., 100 µM photolytically released glutamate) reflected ensemble receptors mostly from the closed-channel receptor population, yet $k_{cl}$ reflected the open-channel conformation (see Equations 5-7 below).

The results from the binding site assessment and the kinetic characterization of the effect of AF44/AF42 on both $k_{cl}$ and $k_{op}$ as well as the amplitude measurement were all consistent with the conclusion that AF44/AF42 is a noncompetitive inhibitor selective to the GluA2 closed-channel conformation.

Pharmaceutical Compositions

The aptamers of the present invention provide a class of water-soluble, high affinity compounds that inhibit AMPA-type glutamate ion channels but do not inhibit glutamate binding to the AMPA glutamate receptor. Non-competitive inhibitors such as these are useful as biochemical probes for structure-function studies and as potential therapeutic agents for a number of neurological disorders and diseases.

Accordingly, the present invention also includes pharmaceutical compositions comprising the nucleic acid aptamers of the invention. In some embodiments, the compositions are suitable for internal use and include an effective amount of a pharmacologically active compound of the invention, alone or in combination with one or more pharmaceutically acceptable carriers. The compounds are especially useful in that they have very good solubility.

Compositions of the invention can be used in a method for treating a patient or subject having a disease characterized by excessive activation of ionotropic glutamate receptors. Examples of diseases amenable to treatment in accordance with the present invention include amyotrophic lateral sclerosis (ALS), stroke, Alzheimer's disease and Parkinson's syndrome. The method involves administering to the patient or subject a composition comprising a nucleic acid aptamer that binds the receptor involved with the pathology, so that binding of the composition to the target alters the biological function of the target, thereby treating the pathology.

The patient or subject to be treated by the methods of this invention can be a mammal, or more particularly, a human.

In practice, the nucleic acid compounds of the invention, are administered in amounts which will be sufficient to exert their desired biological activity, e.g., inhibiting excess activation of AMPA receptors. The preparation of pharmaceutical or pharmacological compositions will be known to those of skill in the art in light of the present disclosure. Typically, such compositions may be prepared as injectables, either as liquid solutions or suspensions; solid forms suitable for solution in, or suspension in, liquid prior to injection; as tablets or other solids for oral administration; as time release capsules; or in any other form currently used, including eye drops, creams, lotions, salves, inhalants and the like. The use of sterile formulations, such as saline-based washes, by surgeons, physicians or health care workers to treat a particular area in the operating field may also be particularly useful. Compositions may also be delivered via microdevice, microparticle or sponge.

Upon formulation, therapeutics will be administered in a manner compatible with the dosage formulation, and in such amount as is pharmacologically effective. The formulations are easily administered in a variety of dosage forms, such as the type of injectable solutions described above, but drug release capsules and the like can also be employed.

In this context, the quantity of active ingredient and volume of composition to be administered depends on the host animal to be treated. Precise amounts of active compound required for administration depend on the judgment of the practitioner and are peculiar to each individual.

The magnitude of a prophylactic or therapeutic dose of aptamer in the acute or chronic management of disease will vary with the severity and nature of the condition to be treated and the route of administration. The dose and perhaps the dose frequency will also vary according to the age, body weight and response of the individual patient. It may be necessary to use dosages outside the usual ranges in some cases, as will be apparent to those skilled in the art. Further, it is noted that the clinician or treating physician will know how and when to interrupt, adjust, or terminate therapy in conjunction with individual patient response. The terms "a therapeutically effective amount" and "an amount sufficient to treat conditions characterized by excessive activation of ionotropic glutamate receptors are encompassed by the above-described dosage amounts and dose frequency schedule.

Any suitable route of administration may be employed for providing the patient with an effective dosage of the aptamer of the invention. For example, oral, rectal, parenteral (subcutaneous, intramuscular, intravenous), transdermal, aerosol and like forms of administration may be employed. Dosage forms include tablets, troches, dispersions, suspensions, solutions, capsules, transdermal delivery systems, and the like.

The pharmaceutical compositions of the present invention comprise a nucleic acid AMPA glutamate receptor inhibitor of the invention as the active ingredient, and may also contain a pharmaceutically acceptable carrier, and optionally, other therapeutic ingredients.

Example 1

Receptor Preparation

To ensure that the aptamers to be identified would recognize functional GluA2Q$_{flip}$ AMPA receptors, cDNAs encoding various subunits of glutamate ion channels were used for transient receptor expression in human embryonic kidney (HEK)-293S cells (45). The cell culture, transfection, and preparation of membrane lipids containing functional, intact GluA2Q$_{flip}$ receptors for aptamer selection were carried out according to protocols known in the art. Briefly, GluA2Q$_{flip}$ receptor was transiently expressed in human embryonic kidney (HEK) 293S cells. These cells were co-transfected with the simian virus 40 large T-antigen (TAg) gene to enhance receptor expression, in accordance with materials and methods known to those of skill in the art.

For SELEX, the membrane-bound GluA2Q$_{flip}$ receptors were harvested 48 hours after transfection (45). Specifically, the HEK-293S cells were homogenized briefly in a cold, 50 mM Tris-acetate buffer (pH 7.4) containing 10 mM EDTA and 1 mM phenylmethanesulphonyl fluoride (PMSF). Large membrane pieces were removed by a low-speed spin at 1000 g for 10 min. The supernatant was centrifuged again at >20,000 g for 30 min. The pellet was washed twice with cold 50 mM Tris-acetate buffer (pH7.4). Before using for SELEX, the cell membrane pellet was resuspended in 1× extracellular buffer, which contained (in mM) 145 NaCl, 3 KCl, 1 CaCl$_2$, 1 MgCl$_2$, 10 HEPES (pH 7.4).

Example 2

Aptamer Selection by SELEX

The operation of SELEX is well known in the art and has been described previously supra. In each round of SELEX (a total of 14 cycles were used), a combinatorial RNA library with ~10$^{15}$ random sequences was first dissolved in 1× extracellular buffer (145 mM NaCl, 3 mM KCl, 1 mM CaCl$_2$, 2 mM MgCl$_2$, and 10 mM HEPES pH 7.4). The final concentration of membrane-bound receptor in the binding mix was 8 nM, as determined by [$^3$H]AMPA binding. The binding mixture was incubated at 22° C. for 50 minutes in the presence of 0.3 units/µl RNase inhibitor. For elution, 1 mM (final concentration) of 1-(4-aminophenyl)-3-methylcarbamoyl-4-methyl-7,8-methylenedioxy-3,4-dihydro-5H-2,3-benzodiazepine, which we termed as BDZ-f, was used. The eluted RNAs were subjected to reverse transcription-PCR. To suppress enrichment of nonspecific RNAs bound to any unwanted "targets", such as lipids, three negative selections at rounds 4, 8, and 13 were run in which plain HEK-293 cell membrane fragments lacking only GluA2Q$_{flip}$ receptors were used to absorb nonspecific RNAs. For identifying consensus sequences, the DNA pools from rounds 12 and 14 (i.e., 14 was the final round) were separately cloned into the pGEM-T easy vector (Invitrogen, Carlsbad Calif.) and sequenced.

Figure 1:
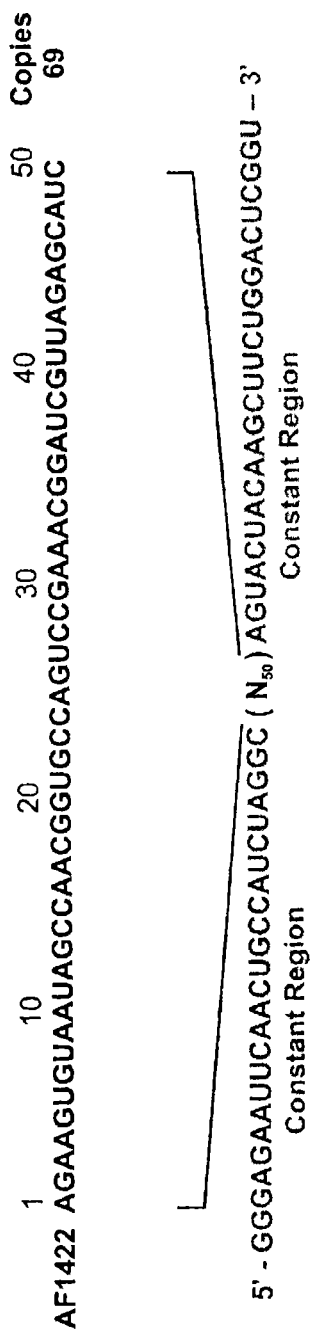
FIG. 1 shows an enriched RNA sequence identified using the SELEX process, and the number of copies from 92 clones; AF1422 (SEQ ID NO: 1) represents the high population of an aptamer that binds the closed-channel conformation of the GluA2Q$_{flip}$ AMPA receptor subunit. AF1422 had a point mutation from GGC to GCC at the 5'-end of constant region next to the variable region.

Four enriched RNA sequences were identified from 92 clones randomly chosen from rounds 12 and 14. One of these is shown in FIG. 1; the name given to the sequence is shown on the left; on the right is the copy number. The variable region, containing 50 nucleotides (or N$_{50}$), is marked in black letters, whereas the 5'- and 3'-constant regions are shown below and indicated in gray. It should be noted that AF1422 had a point mutation from GGC to GCC at the 5'-end constant region next to the variable region, and AF1437 had 7 consecutive nucleotides missing (4 nucleotides within variable region and 3 nucleotides within the 3'-end constant region), from the evolution process.

Whole-Cell Current Recording

The procedure for whole-cell current recording used to assay putative aptamers is known in the art. For the present invention, all recordings were at −60 mV and 22° C. The recording electrode was filled with the buffer (in mM): 110 CsF, 30 CsCl, 4 NaCl, 0.5 CaCl$_2$, 5 EGTA, and 10 HEPES (pH 7.4 adjusted by CsOH). The extracellular buffer composition used is described supra. All other buffers used were previously described. The whole-cell current was recorded using an Axopatch 200B amplifier at a cutoff frequency of 2-20 kHz by a built-in, four-pole Bessel filter and digitized at 5-50 kHz sampling frequency using a Digidata 1322A (Molecular Devices). pClamp 8 (Molecular Devices, Sunnyvale Calif.) was used for data acquisition.

Using whole-cell recording, the putative inhibitory property for each aptamer was tested with HEK 293 cells expressing GluA2Q$_{flip}$ receptors and expressed as the ratio of the whole-cell current amplitude in the absence and presence of an aptamer, that is, A/A(I). The current was recorded at −60 mV, pH 7.4 and 22° C. with the same HEK-293 cell expressing GluA2Q$_{flip}$. Representative traces of the whole-cell current response of GluA2Q$_{flip}$ to 100 µM glutamate in the absence (left panel) and the presence (right panel) of 1 µM of aptamer AF1422 are shown in FIG. 2.

Selected RNA sequences were assayed using whole-cell current recording with GluA2Q$_{flip}$. Again the result was represented by the ratio of the current amplitude in the absence and presence, or A/A(I), of 1 µM aptamer and 100 µM glutamate (shown in FIG. 3). The third round of the library or "pool 3" at 1 µM was used as a control. The '*' indicates P≤0.05 from the two-tailed Student's t test (H$_0$: µ=µ$_0$=1, 1 being the theoretical value of no inhibition, marked as the dashed line).

Example 3

Identification of the Minimal, Functional Aptamer Sequence: AF44 and AF42 Inhibitor Pair Guided by Mfold, an RNA secondary structure prediction program (46), a number of shorter versions of AF1422 were constructed in order to identify the minimal, yet functional RNA sequence (FIG. 4).

To create shorter pieces of RNAs, the predicted secondary structures that were thought to be important were preserved. For example, AF78 was constructed to test whether the stem-loop structure, comprised of the initial 20 or so nucleotides at the 5' constant region, played any functional role. The fact that AF78 turned out to be non-inhibitory suggested that this region was essential for inhibition by AF1422. However, AF20, which contained only this stem loop, was not sufficient to inhibit either alone or together with AF42 as an inhibitory pair.

To create AF44, the projected secondary structure of AF1422 was modified in the following way. First, the stem formed from U19/G99 to U31/G86 was significantly shortened by retaining only three-GC base pairs, i.e., C20/G98, G27/C90 and G30/C87 (see FIG. 4). Second, to maintain the two central loops as in AF1422, nucleotide G22 was replaced with A22 (see FIG. 4) (note that G22 is numbered as the nucleotide position of AF44 in the truncated sequence; in the wild-type AF1422 sequence, it corresponds to G32 in FIG. 4). Without this replacement, the shorter sequence carrying G22 (i.e., AF44 wild-type) showed no activity at all with GluA2 receptor channels when it combined with AF42 (data not shown). This was because the wildtype sequence in AF44 (G22) could no longer fold into the same secondary structure as in the central loop of AF1422 (FIG. 4). Yet, AF44(A22) was projected to fold into a structure resembling the central loop of AF1422 with a shortened stem. Taken together, AF44 and AF42 as a whole entity were considered a minimal, functional inhibitor entity and were used for all the subsequent studies below (for convenience, AF44(A22) was simply termed AF44 in this work).

In contrast to AF20, therefore, AF44, which carries this stem-loop module, was capable of acting with AF42 as an inhibitory pair (FIG. 5). Furthermore, based on the functional combination of AF44 and AF42, a removal of the terminal loop from the AF42 resulting AF38 led to a total loss of function, suggesting that this terminal loop was essential.

By monitoring the A/A(I) value, the inhibitory function of single, but shorter RNA pieces were tested, one at a time, but none were found that worked alone as an inhibitor (FIG. 5). Eventually it was established that the shortest, functional aptamer version of AF1422 was in fact a pair, i.e., AF44 and AF42 (AF44 and AF42 represent a 44-nucleotide (nt) RNA and a 42-nt RNA molecules respectively). In other words, the use of either AF44 or AF42 alone did not render any inhibition; yet, an equal molar mixture of AF44 and AF42 reproduced an inhibition as full as AF1422.

Characterization of the Inhibition Constant of AF44/AF42 with GluA2Q$_{flip}$

A laser-pulse photolysis technique was used to characterize the mechanism of inhibition by measuring the effect of an aptamer on the channel-opening kinetics (29). Briefly, γ-O-(α-carboxy-2-nitrobenzyl)glutamate (caged glutamate) (43) (Invitrogen) with or without aptamer dissolved in the extracellular buffer was applied to a cell using a flow device. A single, 355-nm laser pulse with a pulse length of 8 ns and pulse energy of 200-800 µJ, generated from a pulsed Q-switched Nd:YAG laser (Continuum, Santa Clara, Calif.), was used for photolyzing the caged glutamate. To calibrate the concentration of released glutamate, two solutions of free glutamate with known concentrations were applied to the same cell using the same flow device before and after a laser flash. The current amplitudes obtained from this calibration were compared with the amplitude from the laser measurement with reference to the dose-response relationship for GluA2Q$_{flip}$ (47).

Kinetic Data Analysis: Mechanism of Channel Opening

The opening of the GluA2Q$_{flip}$ channel in response to glutamate binding was kinetically described in a general mechanism:

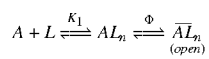

A represents the closed-channel, unliganded form of the receptor, L the ligand, $AL_n$ the closed-channel forms bound with ligands, and $\overline{AL_n}$ the open-channel state, $K_1$ the intrinsic dissociation constant of activating ligand and Φ the channel opening equilibrium constant; n is the number of the ligand molecules that bind to the receptor to open the channel (i.e., n=1-4). Based on this mechanism and also the assumption that the ligand-binding rate was fast as compared with the channel opening rate, the observed rate constant of channel opening ($k_{obs}$) was written as Equation 2.

$$k_{obs} = k_{cl} + k_{op}\left(\frac{L}{K_1 + L}\right)^n \quad \text{(eq. 2)}$$

$$I_t = I_{max}[1 - \exp(-k_{obs}t)] \quad \text{(eq. 3)}$$

In Equation 2, $k_{cl}$ and $k_{op}$ are the channel-closing and channel-opening rate constants, respectively. Furthermore, $k_{obs}$ was calculated from Equation 3, where $I_{max}$ is the maximum current amplitude and $I_t$ is the current amplitude at time t. Our previous studies of AMPA receptors, including a mutant AMPA receptor, for their channel-opening kinetic mechanisms led us to conclude that binding of two glutamate molecules per receptor (i.e., n=2) was sufficient to open the channel (48). Using the laser-pulse photolysis technique, we previously determined the $k_{op}$ of $(8.0\pm0.49)\times10^4$ s$^{-1}$ and the $k_{cl}$ of $(2.6\pm0.20)\times10^3$ s$^{-1}$, respectively, for the channel-opening kinetic constants of the GluA2Q$_{flip}$ receptor.

Kinetic Data Analysis: Mechanism of Inhibition

The noncompetitive mechanism of inhibition was investigated by measuring the effect of an aptamer pair, AF44/AF42, on the channel-opening rate constants (49, 50). By this mechanism (see scheme below), an inhibitor binds to both the closed- and open-channel states through a regulatory site, and the binding results in inhibition of $k_{obs}$ as in Equation 4, where I is the molar concentration of the inhibitor (other symbols have been defined earlier):

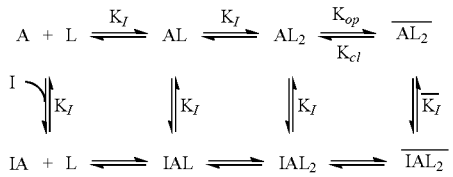

$$k_{obs} = k_{op}\left(\frac{L}{L+K_1}\right)^n\left(\frac{K_I}{K_I+I}\right) + k_{cl}\left(\frac{\overline{K_I}}{\overline{K_I}+I}\right) \quad \text{(eq. 4)}$$

In deriving Equation 4, one inhibitory site was assumed. At low concentrations of glutamate (L<<K$_1$), $k_{obs}$ reflected $k_{cl}$ since the contribution of the $k_{op}$ portion in Equation 4 to the overall rate, $k_{obs}$, was negligible. Thus, Equation 4 was reduced into Equation 5, and the effect of the inhibitor on $k_{cl}$ could be assessed (29) by using Equation 5.

$$k_{obs} = k_{cl}\left(\frac{\overline{K_I}}{\overline{K_I}+I}\right) \quad \text{(eq. 5)}$$

Similarly, the effect of AF44/AF42 on $k_{op}$ was measured at a series of high glutamate concentrations (where $k_{obs}>k_{cl}$).

By noncompetitive inhibition, AF44/AF42 would affect $k_{op}$ (Equation 6), as was observed (FIG. 12, lower panel).

$$k_{obs} - k_{cl}\left(\frac{\overline{K_I}}{K_I + I}\right) = k_{op}\left(\frac{L}{L + K_1}\right)^n \left(\frac{K_I}{K_I + I}\right) \quad \text{(eq. 6)}$$

Because the magnitude of $k_{cl}$ reflects the lifetime ($\tau$) of the open channel (i.e., $\tau=1/k_{cl}$), the effect of an inhibitor on $k_{cl}$ reveals whether or not it inhibits the open-channel conformation or state (29). In contrast, $k_{op}$ reflects the closed-channel state, the effect on $k_{op}$, therefore, reveals whether the inhibitor is effective on the closed-channel state (29). Experimentally, we established that for GluA2Q$_{flip}$, at 100 µM photolytically released glutamate, which we set as the low glutamate concentration, $k_{cl}$ was measured (29, 44). In other words, under this condition or $L << K_1$, Equation 2 is reduced to $k_{obs} \approx k_{cl}$ (29, 44). In contrast, $k_{op}$ could be determined at a glutamate concentration of about 300 µM (29, 44). Correspondingly, the effect of an aptamer on $k_{cl}$ and $k_{op}$ could be separately characterized.

Amplitude Data Analysis

The ratio of the whole-cell current amplitude in the absence and presence of a putative aptamer or A/A(I) as a function of aptamer concentration was used to independently measure inhibition constants (29), as illustrated in Equations 7a and 7b (29). These equations were derived based on the same general mechanism of channel opening described earlier. $K_{I, app}$ is the apparent inhibition constant for the inhibitor;

$$\frac{A}{A(I)} = 1 + I\frac{(\overline{AL_2})}{K_{I,app}} \quad \text{(eq. 7a)}$$

$$(\overline{AL_2}) = \frac{\overline{AL_2}}{A + AL + AL_2 + AL_2} = \frac{L^2}{L^2(1 + \Phi) + 2K_1 L\Phi + K_1^2\Phi} \quad \text{(eq. 7b)}$$

other terms have been defined previously.

According to Equation 7, at low glutamate concentrations (i.e., $L << K_1$), the majority of the receptors were in a closed-channel population. Thus the inhibition constant for the closed-channel conformation or state was determined from A/A(I) vs. inhibitor concentration by Equations 7a and 7b. Likewise, at a saturating ligand concentration (i.e., $L >> K_1$), the majority of the receptors were in the open-channel state. Thus the inhibition constant for the open-channel state was determined. In the case of GluA2Q$_{flip}$, because the EC$_{50}$ of GluA2Q$_{flip}$ with glutamate is 1.3 mM and the channel-opening probability of GluA2Q$_{flip}$ is near unity (47), 100 µM glutamate concentration corresponds to the majority of the channels (i.e., ~96%) being in the closed-channel state (47). At 3 mM glutamate concentration, which is a saturating concentration (47), almost all the channels are in the open state (47). Thus, the $K_I$ value of an aptamer for the open- and closed-channel states of GluA2Q$_{flip}$ was determined using these two glutamate concentrations.

Using Equation 7, we characterized the inhibition constant of AF44/AF42 with GluA2Q$_{flip}$, the selection target. A $K_I$ of 1.5±0.1 µM (the solid line in FIG. 6A) was determined for the closed-channel conformation from a series of aptamer concentrations and at 100 µM glutamate concentration. Yet with the same range of aptamer concentration, AF44/AF42 was ineffective in inhibiting the open-channel conformation (hollow symbol in FIG. 6A). The inhibition by AF44/AF42 became detectable only when its concentration was raised much higher.

Example 4

RNA Purification

All RNA aptamer samples were in vitro transcribed and purified for quantitative assay. An RNA sample dissolved in 1 ml of 10 mM Tris-HCl buffer (pH 7.4) was loaded onto a Q anion exchange column (Bio-Rad, Hercules Calif.). The column was then washed with 25 mM Tris-HCl buffer (pH7.4) for 30 min at a flow rate of 1 ml/min. The aptamer was eluted by running 1.5 M NaCl in 25 mM Tris-HCl buffer at the same flow rate. The aptamer sample was then dialyzed in the extracellular buffer for whole-cell current recording assays.

Example 5

Mechanism of Inhibition/Homologous Competitive Binding Assay

The fact that AF44/AF42 inhibited both the closed-channel and the open-channel conformations of GluA2Q$_{flip}$ observed in the amplitude measurements (FIGS. 6A and 6B), although the inhibition of the latter was considerably less potent, was consistent with a noncompetitive mechanism. If this mechanism was indeed operative, AF44/AF42 would be expected to bind to a noncompetitive site, and such a site would be distinct from the glutamate binding site and would be accessible through both the closed-channel and the open-channel conformations. In fact, in a homologous competition binding experiment (42) in which the non-radiolabeled aptamer (or cold aptamer) was used to compete against the same, but radiolabeled, aptamer (or hot aptamer), AF44 bound to not only the closed-channel conformation (i.e., the unliganded, closed-channel receptor form) but also the open-channel conformation (FIG. 10). Specifically, AF44 bound to the two different receptor conformations with equal affinity, i.e., $K_d$=44±18 nM (FIG. 10 left panel, closed-channel conformation) and $K_d$=48±13 nM (FIG. 10 right panel, open-channel conformation), respectively. Likewise, AF42 was found to bind to both the closed-channel conformation ($K_d$=57±21 nM; FIG. 11, left panel) and the open-channel conformation ($K_d$=44±11 nM; FIG. 11 right panel), respectively. The binding results were consistent with noncompetitive sites, because these sites were supposed to be accessible through both the closed- and the open-channel conformations. The fact that AF44 or AF42 alone did not lead to any inhibition and yet each could bind the receptor further suggested that AF44 and AF42 bound to two different sites (FIGS. 10 and 11). These sites were noncompetitive type because binding to the receptor by either AF44 or AF42 or the full length AF1422 was unaffected in the presence of NBQX, a classic competitive inhibitor (data not shown).

Mechanism of action of AF44/AF42: A laser-pulse photolysis measurement of the effect of AF44/AF42 on the channel-opening rate of GluA2Q$_{flip}$—Using a laser-pulse photolysis technique with ~60 microsecond time resolution (43), the mechanism of inhibition of AF44/AF42 was further characterized by measuring its effect on both $k_{cl}$ and $k_{op}$ of GluA2Q$_{flip}$ (29, 44) (FIG. 12). Specifically in this study, $k_{cl}$ and $k_{op}$ of GluA2Q$_{flip}$ were separately determined at 100 µM and 300 µM glutamate photolytically released by the laser-pulse photolysis of caged glutamate (see the rate equations and quantitative treatment of the kinetic data in Experimental Procedures). The laser-pulse photolysis experiment also permitted us to follow simultaneously both the rate of channel opening and the current amplitude at a given glutamate concentration prior to channel desensitization (29) (FIG. 12).

At 1 µM aptamer concentration and at 300 µM glutamate concentration, AF44/AF42 inhibited $k_{op}$ as compared to the control (FIG. 12 upper panel). This was expected because $k_{op}$ reflected the closed-channel conformation and thus the appearance of an inhibitory effect by the aptamer was consistent with the notion that AF44/AF42 inhibited the closed-channel state.

However, at the same aptamer concentration (i.e., AF44/AF42 of 1 µM) but at 100 µM photolytically released glutamate) where $k_{cl}$ was measured (29, 44), AF44/AF42 did not show an inhibition of $k_{cl}$, although it inhibited the current amplitude (FIG. 12, lower panel). Only at a higher concentration of aptamer was the inhibition of $k_{cl}$ observed, along with further reduction of amplitude (FIG. 13). These results demonstrated that AF44/AF42 had a stronger inhibition towards the close-channel conformation than the open-channel conformation. This conclusion was again consistent with the results described earlier. It should be noted that at a low glutamate concentration (i.e., 100 µM photolytically released glutamate) where $k_{cl}$ was measured (29, 44), the fact that AF44/AF42 inhibited the current amplitude at a low concentration but without inhibiting $k_{cl}$ was plausible because the macroscopic amplitude observed at a low glutamate concentration (i.e., 100 µM photolytically released glutamate) reflected ensemble receptors mostly from the closed-channel receptor population, yet $k_{cl}$ reflected the open-channel conformation (see Equations 5-7).

The results from the binding site assessment (FIGS. 10 and 11) and the kinetic characterization of the effect of AF44/AF42 on both $k_{cl}$ and $k_{op}$ (FIGS. 12 and 13) as well as the amplitude measurement (FIGS. 6, and 9) are all consistent with the conclusion that AF44/AF42 is a noncompetitive inhibitor selective to the GluA2 closed-channel conformation.

Example 6

Cell Culture and Transient Expression of Receptors for Whole-Cell Recording

The original cDNAs in pBlueScript encoding rat GluA1, 2 and 3 AMPA receptors and GluK2 kainate receptor were kindly provided by Steve Heinemann. The GluA4 DNA plasmid was kindly provided by Peter Seeburg. The GluK1 plasmid was kindly provided by Geoffrey Swanson. The cDNAs of all three NMDA receptor subunits were gifts from John Woodward. All DNA plasmids were propagated using *Escherichia coli* host (DH5α) and purified using QIAGEN DNA purification kits.

All of the receptors were transiently expressed in HEK-293S cell. HEK-293S cells were maintained in Dulbecco's modified Eagle's medium (DMEM) supplemented with 10% fetal bovine serum and 1% penicillin in a 37° C., 5% $CO_2$, humidified incubator. Receptors were transiently transfected by using calcium phosphate or lipofectamine 2000 (Invitrogen). The DNA plasmids encoding green fluorescent protein (GFP) and T-antigen (TAg) were cotransfected in HEK-293S cells. GFP was used as a transfection marker for cell recording, and TAg was cotransfected to potentiate the receptor expression at the single-cell level (51). Transfected cells were allowed to grow for 48 hour before they were used for recording.

Example 7

Whole-Cell Current Recording

The procedure for whole-cell current recording to assay the inhibitory property of an RNA aptamer is known to those of skill in the art and has been previously described (47). The electrode for whole-cell recording had a resistance of ~3 MΩ, when filled with the electrode solution (in mM): 110 CsF, 30 CsCl, 4 NaCl, 0.5 $CaCl_2$, 5 EGTA, and 10 HEPES (pH 7.4 adjusted by CsOH). The extracellular buffer composition is described above (see "Receptor Preparation"). For recording of the NMDA channels, the intracellular solution contained (in mM) 140 CsCl, 1 $MgCl_2$, 0.1 EGTA, and 10 HEPES (pH 7.2 adjusted by $Mg(OH)_2$), while the extracellular solution contained (in mM) 135 NaCl, 5.4 KCl, 1.8 $CaCl_2$, 10 glucose and 5 HEPES (pH 7.2 adjusted by NaOH). In the extracellular buffer, 2 µM of glycine was added (glycine was the co-agonist of NMDA receptor) (45). All reagents including aptamer were dissolved in the corresponding extracellular buffer and used. A U-tube flow device (52) was used to apply glutamate in the absence and presence of aptamer to a cell expressing the receptor of interest. The whole-cell current was recorded using an Axopatch-200B amplifier at a cutoff frequency of 2-20 kHz by a built-in, eight-pole Bessel filter and digitized at 5-50 kHz sampling frequency using a Digidata 1322A from Axon Instruments (Molecular Devices, Sunnyvale, Calif.). The pClamp 8 software (Molecular Devices) was used for data acquisition. All whole-cell recordings were at −60 mV and 22° C.

Example 8

Statistical Data Analysis

Unless noted otherwise, each data point, such as A/A(I) value shown in all of the biological functional assay plots or binding data point, was an average of at least three measurements collected from at least three cells. Origin 7 was used for data analysis and plotting. Uncertainties reported refer to standard deviation from the mean. Student's t tests were performed for some of our data. The significance of inhibition was evaluated by a one-sample two-tailed Student's t test with the assumption that $H_0$: $\mu=\mu_0=1$, 1 being the theoretical value of no inhibition and indicated by single ($P\leq 0.05$) or double ($P\leq 0.01$) asterisk sign. The significance of the difference between the open-channel and the closed-channel conformations was evaluated by a two-sample two-tailed Student's t test with the assumption that $H_0$: $\mu_1=\mu_2$ and indicated by single ($P\leq 0.05$) or double ($P\leq 0.01$) asterisk sign.

Example 9

Laser-Pulse Photolysis Measurements

The use of the laser-pulse photolysis technique to measure the channel-opening kinetics has been described ((47)). Briefly, caged glutamate ((43)) (In vitrogen, Carlsbad, Calif.) was dissolved in the extracellular buffer and applied to a cell using a flow device (52) (see below). In the laser-pulse photolysis measurement of channel opening, a single laser pulse at 355 nm with a pulse length of 8 ns was generated from a pulsed Q-switched Nd:YAG laser (Continuum, Santa Clara, Calif.). The pulse energy varied in the range of 200-800 µJ, measured at the end of an optical fiber (300 μm core diameter) into which the laser was coupled. To calibrate the concentration of photolytically released glutamate, we applied two solutions of free glutamate with known concentrations to the same cell before and after a laser flash ((53)). The current amplitudes obtained from this calibration were compared with the amplitude from the laser measurement with reference to the dose-response relationship. These measurements also allowed us to monitor any damage to the receptors and/or the cell for successive laser experiments with the same cell ((47)).

Although the invention has been described in detail for the purposes of illustration, it is understood that such detail is solely for that purpose, and variations can be made therein by those skilled in the art without departing from the spirit and scope of the invention which is defined by the following claims.

REFERENCES

1. Hollmann, M., and Heinemann, S. (1994) *Annu Rev Neurosci* 17, 31-108
2. Seeburg, P. H. (1993) *Trends Neurosci* 16, 359-365
3. Dingledine, R., Borges, K., Bowie, D., and Traynelis, S. F. (1999) *Pharmacol Rev* 51, 7-61
4. Palmer, C. L., Cotton, L., and Henley, J. M. (2005) *Pharmacol Rev.* 57, 253-277.
5. Malinow, R., and Malenka, R. C. (2002) *Annu Rev Neurosci* 25, 103-126
6. Monyer, H., Seeburg, P. H., and Wisden, W. (1991) *Neuron* 6, 799-810
7. Keinanen, K., Wisden, W., Sommer, B., Werner, P., Herb, A., Verdoorn, T. A., Sakmann, B., and Seeburg, P. H. (1990) *Science.* 249, 556-560.
8. Kawahara, Y., Ito, K., Sun, H., Aizawa, H., Kanazawa, I., and Kwak, S. (2004) *Nature.* 427, 801.
9. Zhu, J. J., Esteban, J. A., Hayashi, Y., and Malinow, R. (2000) *Nat. Neurosci.* 3, 1098-1106.
10. Mosbacher, J., Schoepfer, R., Monyer, H., Burnashev, N., Seeburg, P. H., and Ruppersberg, J. P. (1994) *Science* 266, 1059-1062
11. Boulter, J., Hollmann, M., O'Shea-Greenfield, A., Hartley, M., Deneris, E., Maron, C., and Heinemann, S. (1990) *Science* 249, 1033-1037.
12. Pei, W., Huang, Z., Wang, C., Han, Y., Park, J. S., and Niu, L. (2009) *Biochemistry* 48, 3767-3777
13. Li, G., Sheng, Z., Huang, Z., and Niu, L. (2005) *Biochemistry* 44, 5835-5841.
14. Dixon, S. J., and Stockwell, B. R. (2009) *Curr Opin Chem Biol* 13, 549-555
15. Marcaurelle, L. A., and Johannes, C. W. (2008) *Prog Drug Res* 66, 187, 189-216
16. Hruby, V. J. (2009) *J Org Chem* 74, 9245-9264
17. Zappala, M., Grasso, S., Micale, N., Polimeni, S., and De Micheli, C. (2001) *Mini Rev Med Chem* 1, 243-253
18. Solyom, S., and Tarnawa, I. (2002) *Curr Pharm Des* 8, 913-939.
19. Weiser, T. (2005) *Curr Drug Targets CNS Neurol Disord* 4, 153-159.
20. Tuerk, C., and Gold, L. (1990) *Science* 249, 505-510
21. Ellington, A. D., and Szostak, J. W. (1990) *Nature* 346, 818-822
22. Nimjee, S. M., Rusconi, C. P., and Sullenger, B. A. (2005) *Annu Rev Med* 56, 555-583
23. Lomeli, H., Mosbacher, J., Melcher, T., Hoger, T., Geiger, J. R., Kuner, T., Monyer, H., Higuchi, M., Bach, A., and Seeburg, P. H. (1994) *Science* 266, 1709-1713
24. Kuner, T., Beck, C., Sakmann, B., and Seeburg, P. H. (2001) *J Neurosci* 21, 4162-4172.
25. Sommer, B., Kohler, M., Sprengel, R., and Seeburg, P. H. (1991) *Cell* 67, 11-19.
26. Oguro, K., Oguro, N., Kojima, T., Grooms, S. Y., Calderone, A., Zheng, X., Bennett, M. V., and Zukin, R. S. (1999) *J Neurosci* 19, 9218-9227.
27. Kwak, S., and Kawahara, Y. (2005) *J Mol Med* 83, 110-120. Epub 2004 December 2029.
28. Ritz, M., Micale, N., Grasso, S., and Niu, L. (2008) *Biochemistry* 47, 1061-1069
29. Wilson, D. S., and Szostak, J. W. (1999) *Annu Rev Biochem* 68, 611-647
30. Ahmed, A. H., Thompson, M. D., Fenwick, M. K., Romero, B., Loh, A. P., Jane, D. E., Sondermann, H., and Oswald, R. E. (2009) *Biochemistry* 48, 3894-3903
31. Ahmed, A. H., Wang, Q., Sondermann, H., and Oswald, R. E. (2009) *Proteins* 75, 628-637
32. Lunn, M. L., Hogner, A., Stensbol, T. B., Gouaux, E., Egebjerg, J., and Kastrup, J. S. (2003) *J Med Chem* 46, 872-875
33. Jin, R., Banke, T. G., Mayer, M. L., Traynelis, S. F., and Gouaux, E. (2003) *Nat Neurosci* 6, 803-810.
34. Jin, R., Horning, M., Mayer, M. L., and Gouaux, E. (2002) *Biochemistry* 41, 15635-15643.
35. Huang, Z., Pei, W., Jayaseelan, S., Shi, H., and Niu, L. (2007) *Biochemistry* 46, 12648-12655
36. Swillens, S. (1995) *Mol Pharmacol* 47, 1197-1203
37. Wieboldt, R., Gee, K. R., Niu, L., Ramesh, D., Carpenter, B. K., and Hess, G. P. (1994) *Proc Natl Acad Sci USA* 91, 8752-8756
38. Li, G., and Niu, L. (2004) *J Biol Chem* 279, 3990-3997. Epub 2003 November 3910.
39. Li, G., Pei, W., and Niu, L. (2003) *Biochemistry* 42, 12358-12366
40. Pei, W., Ritz, M., McCarthy, M., Huang, Z., and Niu, L. (2007) *J Biol Chem* 282, 22731-22736
41. Niu, L., and Hess, G. P. (1993) *Biochemistry* 32, 3831-3835
42. Niu, L., Abood, L. G., and Hess, G. P. (1995) *Proc Natl Acad Sci USA* 92, 12008-12012
43. Li, G., Oswald, R. E., and Niu, L. (2003) *Biochemistry* 42, 12367-12375.
44. Zuker, M. (2003) *Nucleic Acids Res* 31, 3406-3415.
45. Wenthold, R. J., Petralia, R. S., Blahos, J., II, and Niedzielski, A. S. (1996) *J Neurosci* 16, 1982-1989
46. Erreger, K., Dravid, S. M., Banke, T. G., Wyllie, D. J., and Traynelis, S. F. (2005) *J Physiol* 563, 345-358
47. Sommer, B., Keinanen, K., Verdoorn, T. A., Wisden, W., Burnashev, N., Herb, A., Kohler, M., Takagi, T., Sakmann, B., and Seeburg, P. H. (1990) *Science* 249, 1580-1585
48. Pei, W., Huang, Z., and Niu, L. (2007) *Biochemistry* 46, 2027-2036
49. Koike, M., Tsukada, S., Tsuzuki, K., Kijima, H., and Ozawa, S. (2000) *J Neurosci* 20, 2166-2174.
50. Honore, T., Davies, S, N., Drejer, J., Fletcher, E. J., Jacobsen, P., Lodge, D., and Nielsen, F. E. (1988) *Science* 241, 701-703
51. Huang, Z., Han, Y., Wang, C., and Niu, L. (2010) *Biochemistry* 49, 5790-5798
52. Voss, N. R., and Gerstein, M. (2005) *J Mol Biol* 346, 477-492
53. Goodsell, D. S., and Olson, A. J. (2000) *Annu Rev Biophys Biomol Struct* 29, 105-153
54. Tanaka, Y., Fujii, S., Hiroaki, H., Sakata, T., Tanaka, T., Uesugi, S., Tomita, K., and Kyogoku, Y. (1999) *Nucleic Acids Res* 27, 949-955

We claim:

1. An isolated nucleic acid consisting essentially of the nucleotide sequence of SEQ ID NO: 1, SEQ ID NO: 2, SEQ ID NO: 4 or SEQ ID NO: 5.

2. The isolated nucleic acid of claim 1, wherein said nucleic acid binds to a glutamate ion channel receptor.

3. The isolated nucleic acid of claim 2, wherein said nucleic acid selectively inhibits to a GluA2Q subunit of a glutamate ion channel receptor.

4. The isolated nucleic acid of claim 2, wherein said nucleic acid selectively binds to a GluA2Q subunit of a closed-channel conformation of a glutamate ion channel receptor.

5. The isolated nucleic acid of claim 2, wherein said GluA2Q subunit is a GluA2Q$_{flip}$ subunit.

6. The isolated nucleic acid of claim 2, wherein said glutamate ion channel receptor is an α-amino-3-hydroxyl-5-methyl-4-isoxazole propionic acid (AMPA) receptor.

7. The isolated nucleic acid of claim 1, wherein said nucleic acid is a non-competitive inhibitor of glutamate ion channel receptor activity.

8. The isolated nucleic acid of claim 1, wherein the nucleic acid is RNA.

9. A truncated form of the nucleic acid of claim 1, wherein said isolated nucleic acid contains between 35 and 80 contiguous nucleotides of SEQ ID NO: 1.

10. The isolated nucleic acid of claim 1, wherein said nucleic acid contains one or more chemically modified nucleotides.

11. The isolated nucleic acid of claim 10 wherein the one or more chemically modified nucleotides has a 2' fluoro substituent.

12. The isolated nucleic acid of claim 1, wherein said nucleic acid inhibits glutamate receptor function.

13. The isolated nucleic acid of claim 1, wherein said nucleic acid has a $K_1$ of about 1.5 μM.

14. A nucleic acid composition that inhibits an AMPA receptor comprising:
   (a) an aptamer consisting essentially of the nucleotide sequence of SEQ ID NO. 1;
   (b) an aptamer pair comprising a first aptamer comprising a nucleotide sequence selected from the group consisting of SEQ ID NO: 2, SEQ ID NO: 3 and SEQ ID NO: 4 and a second aptamer comprising a nucleotide sequence selected from the group consisting of SEQ ID NO: 3, SEQ ID NO: 5, and SEQ ID NO. 6; or
   (c) a combination of (a) and (b).

15. An isolated DNA that encodes an RNA comprising a nucleotide sequence selected from the group consisting of SEQ ID NO: 1, SEQ ID NO: 2, SEQ ID NO: 3, SEQ ID NO: 4, SEQ ID NO: 5 and SEQ ID NO: 6.

16. The isolated DNA of claim 15 wherein the RNA comprises the nucleotide sequence corresponding to SEQ ID NO.: 1.

17. A method of inhibiting a glutamate receptor comprising contacting said receptor with the nucleic acid of claim 1.

18. A composition comprising the nucleic acid inhibitor of an AMPA receptor of claim 12 and a pharmaceutically acceptable carrier.

19. A method of treating a disease characterized by excessive activation of ionotropic glutamate receptors comprising administering a therapeutically effective amount of a nucleic acid inhibitor of an AMPA receptor of claim 12.

20. The method of claim 19, wherein the disease is a neurodegenerative disorder selected from the group consisting of amyotrophic lateral sclerosis, stroke, Alzheimer's disease and Parkinson's syndrome.

* * * * *